United States Patent
Davis et al.

(10) Patent No.: US 6,406,705 B1
(45) Date of Patent: Jun. 18, 2002

(54) USE OF NUCLEIC ACIDS CONTAINING UNMETHYLATED CPG DINUCLEOTIDE AS AN ADJUVANT

(75) Inventors: Heather L. Davis, Ottawa (CA); Joachim Schorr, Hilden (DE); Arthur M. Krieg, Iowa City, IA (US)

(73) Assignees: University of Iowa Research Foundation, Iowa City, IA (US); Coley Pharmaceutical GmbH, Langenfield (DE); Ottawa Health Research Institute, Ottawa (CA)

( * ) Notice: Subject to any disclaimer, the term of this patent is extended or adjusted under 35 U.S.C. 154(b) by 0 days.

(21) Appl. No.: 09/325,193

(22) Filed: Jun. 3, 1999

Related U.S. Application Data

(63) Continuation-in-part of application No. 09/154,614, filed as application No. PCT/US98/04703 on Mar. 10, 1998.
(60) Provisional application No. 60/040,376, filed on Mar. 10, 1997.

(51) Int. Cl.$^7$ .......................... A61K 45/00; A61K 39/12
(52) U.S. Cl. ............... 424/278.1; 424/279.1; 424/282.1; 424/204.1; 536/23.72; 930/200; 930/210; 930/220
(58) Field of Search .................. 424/278.1, 279.1, 424/282.1, 204.1; 930/200, 210, 220; 536/23.72

(56) References Cited

U.S. PATENT DOCUMENTS

| | | |
|---|---|---|
| 3,906,092 A | 9/1975 | Hilleman et al. |
| 4,185,090 A | 1/1980 | McIntire ..................... 424/92 |
| 5,248,670 A | 9/1993 | Draper et al. ................. 514/44 |
| 5,585,479 A | 12/1996 | Hoke et al. .................. 536/24.5 |
| 5,663,153 A | 9/1997 | Hutcherson et al. .......... 514/44 |
| 5,723,130 A | 3/1998 | Hancock et al. ......... 424/211.1 |
| 5,723,335 A | 3/1998 | Hutcherson et al. ....... 435/375 |
| 5,750,110 A | 5/1998 | Prieels et al. ............ 424/208.1 |
| 5,786,189 A | 7/1998 | Locht et al. ............. 435/172.3 |
| 6,780,448 | * 7/1998 | Davis .......................... 514/44 |
| 5,849,719 A | 12/1998 | Carson et al. ................. 514/44 |
| 6,180,614 B1 | * 1/2001 | Davis .......................... 514/44 |

FOREIGN PATENT DOCUMENTS

| | | | |
|---|---|---|---|
| EP | 0468520 | 1/1992 | .......... A61K/31/70 |
| EP | 0302758 B1 | 3/1994 | .......... C12N/15/37 |
| WO | WO 91/12811 | 9/1991 | .......... A61K/31/70 |
| WO | WO 92/03456 | 3/1992 | .......... C07H/15/12 |
| WO | WO 92/18522 | 10/1992 | .......... C07H/21/00 |
| WO | WO 92/21353 | 12/1992 | .......... A61K/31/70 |
| WO | WO 94/19945 | 9/1994 | .......... A01N/43/04 |
| WO | WO 95/05853 | 3/1995 | |
| WO | WO 95/26204 | 10/1995 | .......... A61K/48/00 |
| WO | WO 96/02555 | 2/1996 | |
| WO | WO 96/35782 | 11/1996 | |
| WO | WO 97/28259 | 8/1997 | .......... C12N/15/00 |
| WO | WO 98/14210 | 4/1998 | .......... A61K/39/35 |
| WO | WO98/16247 A1 | 4/1998 | |
| WO | WO 98/18810 | 5/1998 | .......... C07H/21/00 |
| WO | WO98/32462 A1 | 7/1998 | |
| WO | WO 98/37919 | 9/1998 | .......... A61K/49/00 |
| WO | WO 98/40100 | 9/1998 | .......... A61K/39/39 |
| WO | WO 98/52581 | 11/1998 | .......... A61K/35/00 |
| WO | WO98/55495 A2 | 12/1998 | |
| WO | WO99/33488 A2 | 7/1999 | |

OTHER PUBLICATIONS

Wagner H(ED). Immunobiology of Bacterial CpG–DNA, Springer Publication 2000, Only pp. 26, and 173, 2000.*

Sparwasser et al, Eur. J. Immunol, vol. 27 (7), pp. 1671–1679, abstract only, Jul. 1997.*

Stull et al., Antigene, Ribozyme, and Aptamer Nucleic Acid Drugs: Progress and Prospects, *Pharmaceutical Res.*, vol. 12, 4:465–483, 1995.

Subramanian et al., Theoretical Considerations on the "Spine of Hydration" in the Minor Groove of d(CGCGAAT-TCGCTG)d(GCGCTTAAGCTGC): Monte Carlo Computer Simulation. *Proc. Nat'l. Acad. Sci. USA*, 85:1836–1840, 1988.

Sun S et al., Mitogenicity of DNA from Different Organisms for Murine B Cells, *The Journal of Immunology*, pp. 3119–3125.

Tanaka T et al., An antisense Oligonucleotide complementary to a sequence in IG2b increases G2b germline transcripts stimulates B cell DNA synthesis and inhibits immunoglobulin secretion. *J. Exp. Med.*, 175:597–607, 1992.

Tang D et al., Genetic immunization is a simple method for eliciting an immune response, *Nature*, vol. 356, pp. 152–154, Mar. 12, 1992.

Thoelen et al., Safety and immunogenicity of a hepatitis B vaccine formulated with a novel adjuvant system, *Vaccine*, vol. 16, No. 17, pp. 708–714, 1998.

Thorne PS., Experimental grain dust atmospheres generated by wet and dry aerosolization techniques. *Am J Ind Med* 25(1):109–12, 1994.

(List continued on next page.)

*Primary Examiner*—Ali R. Salimi
(74) *Attorney, Agent, or Firm*—Wolf, Greenfield & Sacks, P.C.

(57) ABSTRACT

The present invention relates generally to adjuvants, and in particular to methods and products utilizing a synergistic combination of immunostimulatory oligonucleotides having at least one unmethylated CpG dinucleotide (CpG ODN) and a non-nucleic acid adjuvant. Such combinations of adjuvants may be used with an antigen or alone. The present invention also relates to methods and products utilizing immunostimulatory oligonucleotides having at least one unmethylated CpG dinucleotide (CpG ODN) for induction of cellular immunity in infants.

11 Claims, 12 Drawing Sheets

OTHER PUBLICATIONS

Tokunaga T et al., Synthetic Oligonucleotides with Particular Base Sequences form the cDNA Encoding Proteins of *Myobacterium bovis* BCG Induce Interferons and Activate Natural Killer Cells, *Microbiol. Immunol.*, vol. 36, 1:55–66, 1992.

Tokunaga et al., A Synthetic Single–Stranded DNA, Ply (dG, dC), Induces Interferon α/βand –γ, Augments Natural Killer Activity and Suppresses Tumor Growth. *Jpn. J. Cancer Res.*, 79:682–686, Jun. 1988.

Tomasi M et al., Strong mucosal adjuvanticity of cholera toxin within lipid particles of a new multiple emulsion delivery system for oral immunization, *Eur. J. Immunol.*, 27:2720–2725, 1997.

Uhlmann et al., Antisense Oligonucleotides: A New Therapeutic Principle. *Chemical Reviews*, 90:543–584, 1990.

Usinger, A comparison of antibody responses to veterinary vaccine antigens potentiated by different adjuvants, *Vaccine*, vol. 15, No. 17/19, pp. 1902–1907, 1997.

Vosika G et al., Phase I Study of Intravenous Mycobacterial Cell Wall Skeleton and Trehalose Cimycolate Attached To Oil Droplets, *Journal of Biological Response Modifiers*, 3:620–626, 1984.

Vosika G et al., Phase I–II Study of Intralesional Immunotherapy with Oil–Attached *Mycobacterium smegmatis* Cell Wall Skeleton and Trehalose Dimycolate, *Cancer Immunol Immunother*, 6, 135–142 (1979).

Wagner RW, Gene inhibition using antisense oligodeoxynucleotides. *Nature*, 372:L333–335, 1994.

Wallace et al., Oligonucleotide probes for the screening of recombinant DNA libraries. *Methods in Enzymology*, 152:432–442 (1987).

Weiss R., Upping the Antisense Ante: Scientists bet on profits from reverse genetics. *Science*, 139:108–109, 1991.

Whalen R, DNA Vaccines for Emerging Infection Diseases: What If?, *Emerging Infectious Disease*, vol. 2, 3:168–175, 1996.

Wu GY et al., Receptor–mediated gene delivery and expression in vivo. *J. Biol. Chem.*, 263:14621–14624, 1988.

Wu–Pong S., Oligonucleotides; Opportunities for Drug Therapy and Research. *Pharmaceutical Technology*, 18:102–114, 1994.

Yamamoto S et al., DNA from bacteria, but not from vertebrates, induces interferons, activates natural killer cells and inhibits tumor growth. *Microbiol Immunol* 36(9):983–97, 1992.

Yamamoto S et al., In vitro augmentation of natural killer cell activity and production of interferon–alpha/beta and—gamma with deoxyribonucleic acid fraction from *Mycobacterium bovis* BCG. *Jpn. J Cancer Res* 79:866–73, Jul. 1988.

Yamamoto S., Mode of Action of Oligonucleotide Fraction Extracted from *Mycobacterium bovis* BCG, *Kekkaku*, vol. 69, 9:29–32, 1994.

McIntyre KW et al., A sense phosphorothioate oligonucleotide directed to the initiation codon of transcription factor NF–kappa B p65 causes sequence–specific immune stimulation. *Antisense Res Dev* 3(4):309–22, Winter 1993.

Messina et al., The Influence of DNA Structure on the in vitro Stimulation of Murine Lymphocytes by Natural and Synthetic Polynucleotide Antigens. *Cellular Immunology*, 147:148–157, 1993.

Messina et al., Stimulation of in vitro Murine Lymphocyte Proliferation by Bacterial DNA. *J. Immunol.*, vol. 147, 6:1759–1764, Sep. 15, 1991.

Mojcik, C., et al., "Administration of a Phosphorothioate Oligonucleotide Antisense Murine Endogenous Retroviral MCF env Causes Immune Effect in vivo in a Sequence–Specific Manner", *Clinical Immunology and Immunopathology*, (1993), 67:2:130–136.

Mottram et al., A novel CDC2–related protein kinase from leishmania mexicana LmmCRK1 is post–translationally regulated during the life cycle. *J. Biol. Chem.* 268:28, 21044–21052 (Oct. 1993).

Neuzil KM et al., Adjuvants influence the quantitative and qualitative immune response in BALB/c mice immunized with respiratory syncytial virus FG subunit vaccine, *Vaccine*, vol. 15, No. 5, pp. 252–532, 1997.

*New England BIOLABS 1988–1989 Catalog.*

Nyce JW and Metzger WJ, DNA antisense therapy for asthma in an animal model. *Nature* 385:721–725, Feb. 20, 1997.

Pisetsky, D., "Stimulation of in vitro proliferation of murine lymphocytes by synthetic oligodeoxynucleotides", *Molecular Biology Repairs*, (1993) 18:217–221.

Pisetsky et al., Stimulation of Murine Lymphocyte Proliferation by a Phosphorothioate Oligonucleotide with Antisense Activity for Herpes Simplex Virus. *Life Science*, vol. 54, pp. 101–107 (1994).

Pisetsky, The Immunological Properties of DNA, *The Journal of Immunology*, pp. 421–423 (1996).

Pisetsky, Immunological Consequences of Nucleic Acid Therapy, *Antisense Research and Development*, 5:219–225 (1995).

Raz E et al., Preferential induction of a Th1 immune response and inhibition of specific IgE antibody formation by plasmid DNA immunization. *Proc Natl Acad Sci USA* 93(10):5141–5, May 14, 1996.

Ribi E et al., Preparation and Antitumor Activity of Nontoxic Lipid A, *Cancer Immunol Immunother*, 12:91–96, 1982.

Roman M et al., Immunostimulatory DNA sequences functions as T helper–1–promoting adjuvants. *Nat Med* 3(8):849–54, Aug. 1997.

Sato et al., Immunostimulatory DNA Sequences Necessary for Effective Intradermal Gene Immunization, *Science*, vol. 273, pp. 352–354, 1996.

Schnell et al., Identification and characterization of a *Saccharomyces cerevisia* gene (PAR1) conferring resistance to iron chelators. *Eur. J. Biochem.*, 200:487–493.

Schultz N et al., Effect of DETOX as an adjuvant for melanoma vaccine, *Vaccine*, vol. 13, No. 5, pp. 503–508, 1995.

Schwartz DA et al., Endotoxin responsiveness and grain dust–induced inflammation in the lower respiratory tract. *Am. J Physiol* 267(5 Pt 1):L609–17, 1994.

Schwartz DA et al., The role of endotoxin in grain dust–induced lung disease. *Am J Respir Crit Care Med* 152(2):603–8, 1995.

Schwartz DA et al., CpG motifs in bacterial DNA cause inflammation in the lower respiratory tract. *J. Clin Invest* 100(1):68–73, Jul. 1, 1997.

Shirakawa T et al., The inverse association between tuberculin responses and atopic disorder. *Science* 275(5296):77–9, Jan. 3, 1997.

Sparwasser T et al., Macrophages sense pathogens via DNA motifs: induction of tumor necrosis factor–alpha–mediated shock. *Eur J Immunol* 27(7):1671–9, Jul. 1997.

Stein CA et al., Oligonucleotides as inhibitors of gene expression: a review. *Cancer Research,* 48:2659–2668, 1988.

Kline JN et al., Immune redirection by CpG oligonucleotides. Conversion of a Th2 response to a Th1 response in a murine model of asthma. *J Invest Med* 45(3):282A, 1997.

Kline JN et al., CpG oligonucleotides can reverse as well as prevent Th2–mediated inflammation in a murine model of asthma. *J Invest Med* 45(7):298A, 1997.

Klinman DM et al., Contribution of CpG Motifs to the Immunogenicity of DNA Vaccines, *The Journal of Immunology,* 158:3635–3639, 1997.

Klinman DM et al., CpG motifs present in bacteria DNA rapidly induce lymphocytes to secrete interleukin 6, interleukin 12, and interferon gamma. *Proc Natl Acad Sci USA* 93(7):2879–83, 1996.

Krieg AM, An innate immune defense mechanism based on the recognition of CpG motifs in microbial DNA. *J Lab Clin Med* 128(2):128–33, 1996.

Krieg AM et al., Uptake of oligodeoxyribonucleotides by lymphoid cells is heterogeneous and inducible. *Antisense Res Dev* 1(2):161–71, Summer 1991.

Krieg AM et al., Oligodeoxynucleotide modifications determine the magnitude of B cell stimulation by CpG motifs. *Antisense Nucleic Acid Drug Dev.* 6(2):133–9, Summer 1996.

Krieg AM et al., "Modification of antisense phosphodiester oligodeoxynucleotides by a 5' cholesteryl moiety increases cellular association and improves efficacy", *Proc. Natl. Acad. Sci.,* (1993), 90:1048–1052.

Krieg AM et al., "CpG DNA: A Pathogenic Factor in Systemic Lupus Erythematosus?", *Journal of Clinical Immunology,* (1995) 15:6:284–292.

Krieg AM et al, Phosphorothioate Oligodeoxynucleotides: Antisense or Anti–Protein?, *Antisense Research and Development,* (1995), 5:241.

Krieg AM et al., "Leukocyte Stimulation by Oligodeoxynucleotides", *Applied Antisense Oligonucleotide Technology,* (1998), 431–448.

Krieg AM et al., CpG motifs in bacterial DNA trigger direct B–cell activation. *Nature* 374:546–9, 1995.

Krieg AM et al, "The role of CpG dinuleotides in DNA vaccines", Trends in Microbiology, vol. 6, pp. 23–27, Jan. 1998.

Krieg AM et al, A Role for Endogenous Retroviral Sequences in the Regulation of Lymphocyte Activation, the Journal of Immunology, vol. 143, 2448–2451.

Kuramoto et al., Oligonucleotide Sequences Required for Natural Killer Cell Activation, *Jpn. J. Cancer Res.,* 83:1128–1131, Nov. 1992.

Leonard et al., Conformation of Guanine 8–Oxoadenine Base Pairs in the Crystal Structure of d(CGCGAATT(08A)GCG). *Biochemistry,* 31(36):8415–8420, 1992.

Lipford GB et al., Bacterial DNA as immune cell activator, *Trends Microbiol,* 6(12): 496–500, Dec. 1998.

Lowell et al., Proteosomes, Emulsomes, and Cholera Toxin B Improve Nasal Immunogenicity of Human Immunodeficiency Virus gp160 in Mice: Induction of Serum, Intestinal, Vaginal, and Lung IgA and IgG, *The Journal of Infectious Diseases,* 175:292–301, 1997.

Macfarlane DE and Manzel L, Antagonism of immunostimulatory CpG–oligodeoxynucleotides by quinacrine, chloroquine, and structurally related compounds. *J Immunol* 160(3):1122–31, Feb. 1, 1998.

Mallon et al., Comparison of antibody response by use of synthetic adjuvant system and Freund complete adjuvant in rabbits, *Am J Vet Res,* vol. 52, No. 9, pp. 1503–1506, Sep. 1991.

Mannino RJ et al., Lipid Matrix–Based Vaccines for Mucosal and Systemic Immunization, pp. 363–387.

Mastrangelo et al. *Seminar in Oncology.* vol. 23, 1:4–21, 1996.

Matson S and Krieg AM, Nonspecific suppression of [3H] thymidine incorporation by "control" oligonucleotides. *Antisense Res Dev* 2(4):325–30, Winter 1992.

Crosby et al., The Early Responses Gene FGFI–C Encodes a Zinc Finger Transcriptional Activator and is a Member of the GCGGGGGCG (GSG) Element–Binding Protein Family. *Mol. Cell. Biol.,* 2:3835–3841, 1991.

Crystal, Transfer of Genes to Humans: Early Lessons and Obstacles to Success. *Science,* vol. 270, pp. 404–410, 1995.

D'Andrea A et al., Interleukin 10 (IL–10) inhibits human lymphocyte interferon gamma–production by suppressing natural killer cell stimulatory factor/IL–12 synthesis in accessory cells. *J Exp Med* 178(3):1041–8, 1993.

Englisch et al., Chemically Modified Oligonucleotides as Probes and Inhibitors, *Angew. Chem. Int. Ed. Engl.,* 30:613–629, 1991.

Erb KJ et al., Infection of mice with Mycobacterium bovis--Bacillus Calmette–Guerin (BCG) suppresses allergen–induced airway eosinophilia. *J Exp Med* 187(4):561–9, Feb. 16, 1998.

Etlinjer, Carrier sequence selection—one key to successful vaccines, *Immunology Today,* vol. 13, 2:52–55, 1992.

Fox RI, Mechanism of action of hydroxychloroquine as an antirheumatic drug. *Chemical Abstracts,* 120:15, Abstract No. 182630 (Apr. 29, 1994).

Gordon et al., Safety, Immunogenicity, and Efficacy of a Recombinantly Produced *Plasmodium falciparum* Circumsporozoite Protein–Hepatitis B Surface Antigen Subunit Vaccine, *JID,* 171, pp. 1576–1585, Jun. 1995.

Gura T., Antisense has Growing Pains. *Science* (1995), 270:575–576.

Hadden J et al., Immunostimulants. *TIPS,* (1993), 141:169–174.

Hadden J et al., Immunopharmacology, *JAMA,* (1992) 268:20:2964–2969.

Halpern MD et al., Bacterial DNA induces murine interferon–gamma production by stimulation of interleukin–12 and tumor necrosis factor–alpha. *Cell Immunol* 167(1):72–8, 1996.

Hatzfeld J., Release of Early Human Hematopoietic Progenitors from Quiescence by Antisense Transforming Growth Factor β1 or Rb Oligonucleotides, *J. Exp. Med.,* (1991) 174:925–929.

Heppner et al., Safety, Immunogenicity, and Efficacy of *Plasmodium falciparum* Repeatless Circumsporozoite Protein Vaccine Encapsulated in Liposomes, *JID,* 174, pp. 361–366, Aug. 1996.

Highfield PE, Sepsis: The More, the Murkier. *Biotechnology,* 12:828, Aug. 12, 1994.

Hoeffler JP et al., Identification of multiple nuclear factors that interact with cyclic adenosine 3′,5′-monophosphate response element–binding protein and activating trascription factor–2 by protein–protein interactions. *Mol Endocrinol* 5(2):256–66, Feb. 1991.

Iguchi–Ariga SM and Shaffner W, CpG methylation of the cAMP–responsive enhancer/promoter sequence TGACGTCA abolishes specific factor binding as well as transcriptional activation. *Genes Dev* 3(5):612–9, May 1989.

Iverson, P., et al., "Pharmacokinetics of an Antisense Phosphorothioate Oligodeoxynucleotide against reve from Human Immunodeficiency Virus Type 1 in the Adult male Rate Following Single Injections and Continuous Infusion", *Antisense Research and Development*, (1994), 4:43–52.

Ishikawa R et al., IFN induction and associated changes in splenic leukocyte distribution. *J. Immunol* 150(9):3713–27, May 1, 1993.

Jakway JP et al., Growth regulation of the B lymphoma cell line WEHI–231 by anti–immunoglobulin, lipopolysaccharide, and other bacterial products. *J Immunol* 137(7):2225–31, Oct. 1, 1986.

Jaroszewski JW and Cohen JS, Cellular uptake of antisense oligonucleotides. *Adv Drug Delivery Rev* 6(3):235–50 1991.

Kimura Y et al., Binding of Oligoguanylate to Scavenger Receptors Is Required for Oligonucleotides to Augment NK Cell Activity and Induce IFN, *J. Biochem.*, vol. 116, 5:991–994, 1994.

Kline JN et al., CpG motif oligonucleotides are effective in prevention of eosinophilic inflammation in a murine model of asthma. *J. Invest Med* 44(7):380A, 1996.

Adya N et al., Expansion of CREB's DNA recognition specificity by Tax results from interaction with Ala–Ala–Arg at positions 282–284 near the conserved DNA–binding domain of CREB. *Proc Natl Acad Sci USA* 91(12):5642–6, Jun. 7, 1994.

Angier, N., Microbe DNA Seen as Alien By Immune System, *New York Times*, Apr. 11, 1995.

Azad RF et al., Antiviral Activity of a Phosphorothioate Oligonucleotide Complementary to RNA of the Human Cytomegalovirus Major Immediate–Early Region. *Antimicrobial Agents and Chemotherapy*, 37:1945–1954, Sep., 1993.

Azuma, Biochemical and Immunological Studies on Cellular Components of Tubercle Bacilli, *Kekkaku*, vol. 69, 9:45–55, 1992.

Ballas ZK et al., Induction of NK activity in murine and human cells by CpG motifs in oligodeoxynucleotides and bacterial DNA. *J Immunol* 157(5):1840–5, 1996.

Bayever, E., Systemic Administration of a Phosphorothioate Oligonucleotide with a Sequence Complementary to p53 for Acute Myelogenous leukemia and Myelodysplastic Syndrome: Initial Results of a Phase I Trail, *Antisense Res. & Dev.* (1993), 3:383–390.

Bennet RM et al., DNA binding to human leukocytes. Evidence for a receptor–mediated association, internalization, and degradation of DNA. *J. Clin Invest* 76(6):2182–90, 1985.

Berg DJ et al., Interleukin–10 is a central regulator of the response to LPS in murine models of endotoxic shock and the Shwartzman reaction but not endotoxin tolerance. *J Clin Invest* 96(5):2339–47, 1995.

Blanchard DK et al., Interferon–gamma induction by lipopolysaccharide: dependence on interleukin 2 and macrophages. *J Immunol* 136(3):963–70, 1986.

Blaxter et al., Genes expressed in Brugia malayi infective third stage larvae. *Molecular and Biochemical Parasitology*, 77:77–93.

Boggs RT et al., Characterization and modulation of immune stimulation by modified oligonucleotides. *Antisense Nucleic Acid Drug Dev* 7(5):461–71, Oct. 1997.

Branda RF et al., Amplification of antibody production by phosphorothioate oligodeoxynucleotides. *J. Lab Clin Med* 128(3):329–38, Sep. 1996.

Branda et al., Immune Stimulation by an Antisense Oligomer Complementary to the rev gene of HIV–1. *Biochemical Pharmacology*, vol. 45, 10:2037–2043, 1993.

Briskin M et al., Lipopolysaccharide–unresponsive mutant pre–B–cell lines blocked in NF–kappa B activation. *Mol. Cell Biol* 10(1):422–5, Jan. 1990.

Chace, J. et al., Regulation of Differentiation in CD5+ and Conventional B Cells, *Clinical Immunology and Immunopathology*, (1993), 68:3:327–332.

Chang YN et al., The palindromic series I repeats in the simian cytomegalovirus major immediate–early promoter behave as both strong basal enhancers and cyclic AMP response elements. *J Virol* 64(1):264–77, Jan. 1990.

Chu RS et al., CpG oligodeoxynucleotides act as adjuvants that switch on T helper 1 (Th1) immunity. *J. Exp Med* 186(10):1623–31, Nov. 17, 1997.

Corr M et al., Gene Vaccination with Naked Plasmid DNA: Mechanism of CTL Priming, *J. Exp. Med.*, vol. 184, 155–160, Oct. 1996.

Cowdery JS et al., Bacterial DNA induces NK cells to produce IFN–gamma in vivo and increases the toxicity of lipopolysaccharides. *J Immunol* 156(12):4570–5, Jun. 15, 1996.

Yamamoto S et al., Unique Palindromic Sequences in Synthetic Oligonucleotides are Required to Induce INF and Augument INF–Mediated Natural Killer Activity. *J. Immunol.*, vol. 148, 12:4072–4076, Jun. 15, 1992.

Yamamoto T et al., Ability of Oligonucleotides with Certain Palindromes to Induce Interferon Production and Augment Natural Killer Cell Activity is Associated with Their Base Length. *Antisense Res. and Devel.*, 4:119–123, 1994.

Yamamoto et al., Lipofection of Synthetic Oligodeoxyribonucleotide Having a Palindromic Sequence AACGTT to Murine Splenocytes Enhances Interferon Production and Natural Killer Activity. *Microbiol. Immunol.*, vol. 38, 10:831–836, 1994.

Yamamoto T et al., Synthetic Oligonucleotides with Certain Palindomes Stimulate Interferon Production of Human Peripheral Blood Lymphocytes in vitro. *Jpn. J. Cancer Res.*, 85:775–779, 1994.

Yi Ae–Kyung et al., IFN–γ Promotes IL–6 and IgM Secretion in Response to CpG Motifs in Bacterial DNA and Oligonucleotides, *The Journal of Immunology*, pp. 558–564 (1996).

Yi, Ae–Kyung et al., Rapid Immune Activation by CpG Motifs in Bacterial DNA, *The Journal of Immunology*, pp. 5394–5402 (1996).

Zhao Q et al., Stage–specific oligonucleotide uptake in murine bone marrow B–cell precursors. *Blood* 84(11):3660–6, 1 Dec. 1994.

Zhao Q et al., Comparison of cellular binding and uptake of antisense phosphodiester, phosphorothioate, and mixed phosphorothioate and methylphosphonate oligonucleotides. *Antisense Res Dev* 3(1):53–66, Spring 1993.

Daheshia, M., et al., "immune induction and modulation by topical ocular administration of plasmid DNA encoding antigens and cytokines", *Vaccine,* vol. 16, No. 11/12 pp. 1103–1110, 1998.

Davis, H.L., "Plasmid DNA expression systems for the purpose of immunization." *Current Opinion in Biotechnology,* 1997, 8:635–640.

Davis, H.L.., et al., "CpG DNA overcomes hyporesponsiveness to hepatitis B vaccine in orangutans." *Vaccine* 18 (2000) 1920–1924.

Davis, H.L., et al., CpG DNA Is a Potent Enhancer of Specific Immunity in Mice Immunized with Recombinant Hepatitis B Surface Antigen, *Ame. Assoc. of Immun,* 1998, pp. 870–876.

Deml, L., et al., "Immunostimulatory CpG Motifs Trigger a T Helper–1 Immune Response to Human Immunodeficiency Virus Type–1 (HIV–1) gp 160 Envelope Proteins", *Clin Chem Lab Med,* 1999, 37(3):199–204.

Doe, B., et al., "Induction of cytotoxic T lymphocytes by intramuscular immunization with plasmid DNA is facilitated by bone marrow–derived cells", *Proc. Natl. Acad. Sci. USA,* vol. 93, pp. 8578–8583, Aug. 1996.

Jones, T.R. et al., "Synthetic oligodeoxynucleotides containing CpG motifs enhance immunogenicity of a peptide malaria vaccine in Aotus monkeys.", *Vaccine* 17, 1999, 3065–3071.

Kataoka, T. et al., "Antitumor Activity of Synthetic Oligonucleotides with Sequences from cDNA Encoding Proteins of *Mycobacterium bovis* BCG", *Jpn. J. Cancer Res.,* Mar. 1992, vol. 83, 244–247.

Klinman, D.M., et al., "Immune Recognition of Foreign DNA: A Cure for Bioterrorism?", *Immunity,* vol. 11, 123–129, Aug., 1999.

Threadgill, D.S. et al., "Mitogenic synthetic polynucleotide suppress the antibody response to a bacterial polysaccharide", *Vaccine,* 1998, pp. 76–82, vol. 16, No. 1.

Kovarik, J., "CpG Oligodeoxynucleotides Can Circumvent the Th2 Polarization of Neonatal Responses to Vaccines but May Fail to Fully Redirect Th2 Responses Established by Neonatal Priming", *The Journal of Immunology,* 1999, 162: 1611–1617.

Krieg, A.M., "CpG DNA Induces Sustained IL–12 Expression in Vivo and Resistance to *Listeria monocytogenes* Challenge", *The Journal of Immunology,* 1998, 161:2428–2434.

McCluskie, M.J. et al., "Cutting Edge: CpG DNA Is a Potent Enhancer of Systemic and Mucosal Immune Responses Against Hepatitis B Surface Antigen with Intranasal Administration to Mice", *J. of Immunology,* 1998, 4463–4465.

Moldoveanu, Z. et al., "CpG DNA, a novel immune enhancer for systemic and mucosal immunization with influenza virus", *Vaccine,* vol. 16 No. 11/12 pp. 1216–1224, 1998.

Quddus, J., et al., "Treating Activated $CD4^+T$ Cells with Either of Two Distinct DNA Methyltransferase Inhibitors, 5–Azacytidine or Procainamide, Is Sufficient to Cause a Lupus–like Disease in Syngeneic Mice" *J. of Clin. Inv., Inc.,* vol. 92, Jul. 1993, 38–53.

Davis, et al., *Proc. Natl. Acad. Sci.* USA, 93(14):7231–8, 1996.

Prince, et al., *Vaccine* 15(8):916–9, 1997.

* cited by examiner

DNA VS PROTEIN IMMUNIZATION IN
NEONATAL (7 DAY OLD) BALB/c MICE

EFFECT OF ADJUVANT ON AB ISOTOPE

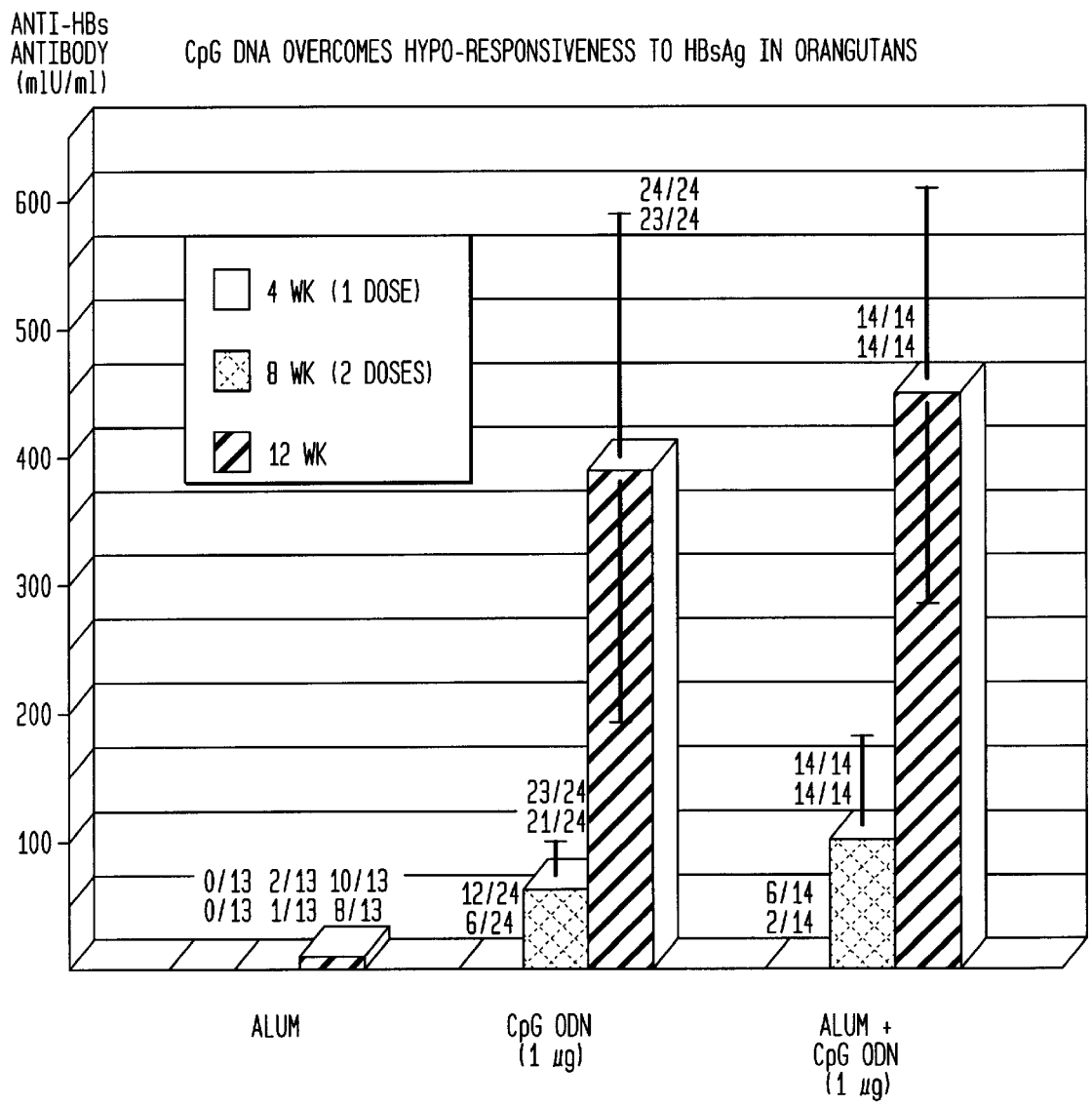

SEQUENCE LISTING

```
<160> NUMBER OF SEQ ID NOS:  98

<210> SEQ ID NO 1
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 1
gctagacgtt agcgt                                                           15

<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
gctagatgtt agcgt                                                           15

<210> SEQ ID NO 3
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<223> OTHER INFORMATION: Synthetic Oligonucleotide

<400> SEQUENCE: 3
gctagacgtt agcgt                                                           15

<210> SEQ ID NO 4
<211> LENGTH: 15
<212> TYPE: DNA
<213> ORGANISM: Artificial Sequence
<220> FEATURE:
<221> NAME/KEY: modified_base
<222> LOCATION: (13)...(13)
<223> OTHER INFORMATION: m5c
```

-continued

```
<223> OTHER INFORMATION: Synthetic Oligonucleotide

<400> SEQUENCE: 4
gctagacgtt agcgt                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 5
gcatgacgtt gagct                                                    15

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
atggaaggtc cagcgttctc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
atcgactctc gagcgttctc                                               20

<210> SEQ ID NO 8
<211> LENGTH: 20
<212> TYPE: DNA
<213> ORGANISM: Artificial Sequence
<220> FEATURE:
<221> NAME/KEY: modified_base
<222> LOCATION: (3)...(3)
<223> OTHER INFORMATION: m5c
<223> OTHER INFORMATION: Synthetic Oligonucleotide

<400> SEQUENCE: 8
atcgactctc gagcgttctc                                               20

<210> SEQ ID NO 9
<211> LENGTH: 20
<212> TYPE: DNA
<213> ORGANISM: Artificial Sequence
<220> FEATURE:
<221> NAME/KEY: modified_base
<222> LOCATION: (18)...(18)
<223> OTHER INFORMATION: m5c
<223> OTHER INFORMATION: Synthetic Oligonucleotide

<400> SEQUENCE: 9
atcgactctc gagcgttctc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 10
atggaaggtc caacgttctc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
gagaacgctg gaccttccat                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
gagaacgctc gaccttccat                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
gagaacgctc gaccttcgat                                              20

<210> SEQ ID NO 14
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<223> OTHER INFORMATION: Synthetic Oligonucleotide

<400> SEQUENCE: 14
gagaacgctg gaccttccat                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
gagaacgatg gaccttccat                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
gagaacgctc cagcactgat                                              20
```

```
<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
tccatgtcgg tcctgatgct                                          20

<210> SEQ ID NO 18
<211> LENGTH: 20
<212> TYPE: DNA
<213> ORGANISM: Artificial Sequence
<220> FEATURE:
<221> NAME/KEY: modified_base
<222> LOCATION: (12)...(12)
<223> OTHER INFORMATION: m5c
<223> OTHER INFORMATION: Synthetic Oligonucleotide

<400> SEQUENCE: 18
tccatgtcgg tcctgatgct                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
tccatgacgt tcctgatgct                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
tccatgtcgg tcctgctgat                                          20

<210> SEQ ID NO 21
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 21 tcaacgtt                                                        8

<210> SEQ ID NO 22
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 22 tcagcgct                                                        8

<210> SEQ ID NO 23
<211> LENGTH: 8
```

```
<212> TYPE: DNA
<213> ORGANISM: Artificial Sequence
<220> FEATURE:
<223> OTHER INFORMATION: Synthetic Oligonucleotide

<400> SEQUENCE: 23 tcatcgat                                                                     8

<210> SEQ ID NO 24
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 24 tcttcgaa                                                                     8

<210> SEQ ID NO 25
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 25 caacgtt                                                                      7

<210> SEQ ID NO 26
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 26 ccaacgtt                                                                     8

<210> SEQ ID NO 27
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 27 aacgttct                                                                     8

<210> SEQ ID NO 28
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 28 tcaacgtc                                                                     8

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
```
atggactctc cagcgttctc                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
atggaaggtc caacgttctc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
atcgactctc gagcgttctc                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
atggaggctc catcgttctc                                              20

<210> SEQ ID NO 33
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<223> OTHER INFORMATION: Synthetic Oligonucleotide

<400> SEQUENCE: 33
atcgactctc gagcgttctc                                              20

<210> SEQ ID NO 34
<211> LENGTH: 20
<212> TYPE: DNA
<213> ORGANISM: Artificial Sequence
<220> FEATURE:
<221> NAME/KEY: modified_base
<222> LOCATION: (18)...(18)
<223> OTHER INFORMATION: m5c
<223> OTHER INFORMATION: Synthetic Oligonucleotide

<400> SEQUENCE: 34
atcgactctc gagcgttctc                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
tccatgtcgg tcctgatgct                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tccatgccgg tcctgatgct                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
tccatggcgg tcctgatgct                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tccatgacgg tcctgatgct                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
tccatgtcga tcctgatgct                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tccatgtcgc tcctgatgct                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
tccatgtcgt ccctgatgct                                               20

<210> SEQ ID NO 42
<211> LENGTH: 20
<212> TYPE: DNA
<213> ORGANISM: Artificial Sequence
<220> FEATURE:

```
<223> OTHER INFORMATION: Synthetic Oligonucleotide

<400> SEQUENCE: 42
tccatgacgt gcctgatgct                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
tccataacgt tcctgatgct                                          20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
tccatgacgt ccctgatgct                                          20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
tccatcacgt gcctgatgct                                          20

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 46
ggggtcaacg ttgacgggg                                           19

<210> SEQ ID NO 47
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 47
ggggtcagtc gtgacgggg                                           19

<210> SEQ ID NO 48
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 48
gctagacgtt agtgt                                               15
```

-continued

```
<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
tccatgtcgt tcctgatgct                                             20

<210> SEQ ID NO 50
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 50
accatggacg atctgtttcc cctc                                        24

<210> SEQ ID NO 51
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 51
tctcccagcg tgcgccat                                               18

<210> SEQ ID NO 52
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 52
accatggacg aactgtttcc cctc                                        24

<210> SEQ ID NO 53
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 53
accatggacg agctgtttcc cctc                                        24

<210> SEQ ID NO 54
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 54
accatggacg acctgtttcc cctc                                        24

<210> SEQ ID NO 55
<211> LENGTH: 24
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 55
accatggacg tactgtttcc cctc                                           24

<210> SEQ ID NO 56
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 56
accatggacg gtctgtttcc cctc                                           24

<210> SEQ ID NO 57
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 57
accatggacg ttctgtttcc cctc                                           24

<210> SEQ ID NO 58
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 58
cacgttgagg ggcat                                                     15

<210> SEQ ID NO 59
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 59
tcagcgtgcg cc                                                        12

<210> SEQ ID NO 60
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 60
atgacgttcc tgacgtt                                                   17

<210> SEQ ID NO 61
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 61
tctcccagcg ggcgcat                                                   17

<210> SEQ ID NO 62
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 62
tccatgtcgt tcctgtcgtt                                                  20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
tccatagcgt tcctagcgtt                                                  20

<210> SEQ ID NO 64
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 64
tcgtcgctgt ctccccttct t                                                21

<210> SEQ ID NO 65
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 65
tcctgacgtt cctgacgtt                                                   19

<210> SEQ ID NO 66
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 66
tcctgtcgtt cctgtcgtt                                                   19

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
tccatgtcgt ttttgtcgtt                                                  20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
```

-continued tcctgtcgtt ccttgtcgtt                                          20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
tccttgtcgt tcctgtcgtt                                          20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
tcctgtcgtt ttttgtcgtt                                          20

<210> SEQ ID NO 71
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 71
tcgtcgctgt ctgcccttct t                                        21

<210> SEQ ID NO 72
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 72
tcgtcgctgt tgtcgtttct t                                        21

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
tccatgcgtg cgtgcgtttt                                          20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
tccatgcgtt gcgttgcgtt                                          20

<210> SEQ ID NO 75
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 75
tccacgacgt tttcgacgtt                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
tcgtcgttgt cgttgtcgtt                                               20

<210> SEQ ID NO 77
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 77
tcgtcgtttt gtcgttttgt cgtt                                          24

<210> SEQ ID NO 78
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 78
tcgtcgttgt cgttttgtcg tt                                            22

<210> SEQ ID NO 79
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 79
gcgtgcgttg tcgttgtcgt t                                             21

<210> SEQ ID NO 80
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 80
tgtcgtttgt cgtttgtcgt t                                             21

<210> SEQ ID NO 81
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 81
tgtcgttgtc gttgtcgttg tcgtt                                         25
```

```
<210> SEQ ID NO 82
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 82
tgtcgttgtc gttgtcgtt                                              19

<210> SEQ ID NO 83
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 83
tcgtcgtcgt cgtt                                                   14

<210> SEQ ID NO 84
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 84
tgtcgttgtc gtt                                                    13

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
tccatagcgt tcctagcgtt                                             20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
tccatgacgt tcctgacgtt                                             20

<210> SEQ ID NO 87
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 87 gtcgyt                                                             6

<210> SEQ ID NO 88
<211> LENGTH: 7
<212> TYPE: DNA
<213> ORGANISM: Artificial Sequence
<220> FEATURE:
<223> OTHER INFORMATION: Synthetic Oligonucleotide
```

```
<400> SEQUENCE: 88 tgtcgyt                                                                7

<210> SEQ ID NO 89
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 89
agctatgacg ttccaagg                                                   18

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
tccatgacgt tcctgacgtt                                                 20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
atcgactctc gaacgttctc                                                 20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
tccatgtcgg tcctgacgca                                                 20

<210> SEQ ID NO 93
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 93 tcttcgat                                                               8

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
ataggaggtc caacgttctc                                                 20

<210> SEQ ID NO 95
```

```
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 95 gtcgtt                                                                    6

<210> SEQ ID NO 96
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 96 gtcgtc                                                                    6

<210> SEQ ID NO 97
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 97 tgtcgtt                                                                   7

<210> SEQ ID NO 98
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 98 tgtcgct                                                                   7
```

USE OF NUCLEIC ACIDS CONTAINING UNMETHYLATED CPG DINUCLEOTIDE AS AN ADJUVANT

RELATED APPLICATIONS

This application is a continuation in part of U.S. patent application Ser. No. 09/154,614 filed on Sep. 16, 1998, pending, which is a National Stage filing of PCT/US98/04703, filed on Mar. 10, 1998, claiming priority to U.S. Provisional Patent Application 60/040,376, filed Mar. 10, 1997, now abandoned.

FIELD OF THE INVENTION

The present invention relates generally to adjuvants, and in particular to methods and products utilizing a synergistic combination of oligonucleotides having at least one unmethylated CpG dinucleotide (CpG ODN) and a non-nucleic acid adjuvant.

BACKGROUND OF THE INVENTION

Bacterial DNA, but not vertebrate DNA, has direct immunostimulatory effects on peripheral blood mononuclear cells (PBMC) in vitro (Krieg et al., 1995). This lymphocyte activation is due to unmethylated CpG dinucleotides, which are present at the expected frequency in bacterial DNA ($1/16$), but are under-represented (CpG suppression, $1/50$ to $1/60$) and methylated in vertebrate DNA. Activation may also be triggered by addition of synthetic oligodeoxynucleotides (ODN) that contain an unmethylated CpG dinucleotide in a particular sequence context. It appears likely that the rapid immune activation in response to CpG DNA may have evolved as one component of the innate immune defense mechanisms that recognize structural patterns specific to microbial molecules.

CpG DNA induces proliferation of almost all (>95%) B cells and increases immunoglobulin (Ig) secretion. This B cell activation by CpG DNA is T cell independent and antigen non-specific. However, B cell activation by low concentrations of CpG DNA has strong synergy with signals delivered through the B cell antigen receptor for both B cell proliferation and Ig secretion (Krieg et al., 1995). This strong synergy between the B cell signaling pathways triggered through the B cell antigen receptor and by CpG DNA promotes antigen specific immune responses. In addition to its direct effects on B cells, CpG DNA also directly activates monocytes, macrophages, and dendritic cells to secrete a variety of cytokines, including high levels of IL-12 (Klinman et al., 1996; Halpern et al., 1996; Cowdery et al., 1996). These cytokines stimulate natural killer (NK) cells to secrete gamma-interferon (IFN-γ-) and have increased lytic activity (Klinman et al., 1996, supra; Cowdery et al., 1996, supra; Yamamoto et al., 1992; Ballas et al., 1996). Overall, CpG DNA induces a Th1 like pattern of cytokine production dominated by IL-12 and IFN-γ with little secretion of Th2 cytokines (Klinman et al., 1996).

Hepatitis B virus (HBV) poses a serious world-wide health problem. The current HBV vaccines are subunit vaccines containing particles of HBV envelope protein(s) which include several B and T cell epitopes known collectively as HBV surface antigen (HBsAg). The HBsAg particles may be purified from the plasma of chronically infected individuals or more commonly are produced as recombinant proteins. These vaccines induce antibodies against HBsAg (anti-HBs), which confer protection if present in titers of at least 10 milli-International Units per milliliter (mIU/ml) (Ellis, 1993). The current subunit vaccines whch contain alum (a Th2 adjuvant), are safe and generally efficacious. They, however, fail to meet all current vaccination needs. For example, early vaccination of infants born to chronically infected mothers, as well as others in endemic areas, drastically reduces the rate of infection, but a significant proportion of these babies will still become chronically infected themselves (Lee et al., 1989; Chen et al., 1996). This could possibly be reduced if high titers of anti-HBs antibodies could be induced earlier and if there were HBV-specific CTL. In addition, there are certain individuals who fail to respond (non-responders) or do not attain protective levels of immunity (hypo-responders). Finally, there is an urgent need for an effective treatment for the estimated 350 million chronic carriers of HBV and a therapeutic vaccine could meet this need.

SUMMARY OF THE INVENTION

The present invention relates to methods and products for inducing an immune response. The invention is useful in one aspect as a method of inducing an antigen specific immune response in a subject. The method includes the steps of administering to the subject in order to induce an antigen specific immune response an antigen and a combination of adjuvants, wherein the combination of adjuvants includes at least one oligonucleotide containing at least one unmethylated CpG dinucleotide and at least one non-nucleic acid adjuvant, and wherein the combination of adjuvants is administered in an effective amount for inducing a synergistic adjuvant response. In one embodiment the subject is an infant.

The CpG oligonucleotide and the non-nucleic acid adjuvant may be administered with any or all of the administrations of antigen. For instance the combination of adjuvants may be administered with a priming dose of antigen. In another embodiment the combination of adjuvants is administered with a boost dose of antigen. In some embodiments the subject is administered a priming dose of antigen and oligonucleotide containing at least one unmethylated CpG dinucleotide before the boost dose. In yet other embodiments the subject is administered a boost dose of antigen and oligonucleotide containing at least one unmethylated CpG dinucleotide after the priming dose.

The antigen may be any type of antigen known in the art. For example, the antigen may be selected from the group consisting of peptides, polypeptides, cells, cell extracts, polysaccharides, polysaccharide conjugates, lipids, glycolipids and carbohydrates. Antigens may be given in a crude, purified or recombinant form and polypeptide/peptide antigens, including peptide mimics of polysaccharides, may also be encoded within nucleic acids. Antigens may be derived from an infectious pathogen such as a virus, bacterium, fungus or parasite, or the antigen may be a tumor antigen, or the antigen may be an allergen.

According to another aspect of the invention a method of inducing a Th1 immune response in a subject is provided. The method includes the step of administering to the subject in order to induce a Th1 immune response a combination of adjuvants, wherein the combination of adjuvants includes at least one oligonucleotide containing at least one unmethylated CpG dinucleotide and at least one non-nucleic acid adjuvant, and wherein the combination of adjuvants is administered in an effective amount for inducing a Th1 immune response. In one embodiment the combination of adjuvants is administered simultaneously. In another embodiment the combination of adjuvants is administered sequentially. In some embodiments the combination of adjuvants is administered in an effective amount for inducing a synergistic Th1 immune response. In another aspect, the same method is performed but the subject is an infant and the Th1 response can be induced using CpG DNA alone, or CpG DNA in combination with a non-nucleic acid adjuvant at the same or different site, at the same or different time.

The invention in other aspects is a composition of a synergistic combination of adjuvants. The composition includes an effective amount for inducing a synergistic adjuvant response of a combination of adjuvants, wherein the combination of adjuvants includes at least one oligonucleotide containing at least one unmethylated CpG dinucleotide and at least one non-nucleic acid adjuvant. The composition may also include at least one antigen, which may be selected from the group consisting of peptides, polypeptides, cells, cell extracts, polysaccharides, polysaccharide conjugates, lipids, glycolipids and carbohydrates. Antigens may be given in a crude, purified or recombinant form and polypeptide/peptide antigens, including peptide mimics of polysaccharides, may also be encoded within nucleic acids. Antigens may be derived from an infectious pathogen such as a virus, bacterium, fungus or parasite, or the antigen may be a tumor antigen, or the antigen may be an allergen.

According to other aspects the invention includes a method for immunizing an infant. The method involves the step of administering to an infant an antigen and an oligonucleotide containing at least one unmethylated CpG dinucleotide and at least one non-nucleic acid adjuvant in an effective amount for inducing cell mediated immunity or Th1-like responses in the infant. The method may also involve the step of administering at least one non-nucleic acid adjuvant.

The CpG oligonucleotide may be administered with any or all of the administrations of antigen. For instance the CpG oligonucleotide or the combination of adjuvants may be administered with a priming dose of antigen. In another embodiment the CpG oligonucleotide or the combination of adjuvants is administered with a boost dose of antigen. In some embodiments the subject is administered a priming dose of antigen and oligonucleotide containing at least one unmethylated CpG dinucleotide before the boost dose. In yet other embodiments the subject is administered a boost dose of antigen and oligonucleotide containing at least one unmethylated CpG dinucleotide after the priming dose.

The invention in other aspects includes a method of inducing a stronger Th1 immune response in a subject being treated with a non-nucleic acid adjuvant. The method involves the steps of administering to a subject receiving an antigen and at least one non-nucleic acid adjuvant and at least one oligonucleotide containing at least one unmethylated CpG dinucleotide in order to induce a stronger Th1 immune response than either the adjuvant or oligonucleotide produces alone.

The invention in other aspects include a method of inducing a non-antigen-specific Th1-type immune response, including Th1 cytokines such as IL-12 and IFN-γ, for temporary protection against various pathogens including viruses, bacteria, parasites and fungi. The method involves the steps of administering to a subject at least one non-nucleic acid adjuvant and at least one oligonucleotide containing at least one unmethylated CpG dinucleotide in order to induce a Th1 innate immune response. For longer term protection, these adjuvants may be administered more than once. In another embodiment, CpG DNA may be used alone at one or more of the administrations.

In each of the above described embodiments a CpG oligonucleotide is used as an adjuvant. The oligonucleotide in one embodiment contains at least one unmethylated CpG dinucleotide having a sequence including at least the following formula:

wherein C and G are unmethylated, wherein $X_1X_2$ and $X_3X_4$ are nucleotides. In one embodiment the 5'$X_1X_2$CG$X_3$ $X_4$ 3' sequence is a non-palindromic sequence.

The oligonucleotide may be modified. For instance, in some embodiments at least one nucleotide has a phosphate backbone modification. The phosphate backbone modification may be a phosphorothioate or phosphorodithioate modification. In some embodiments the phosphate backbone modification occurs on the 5' side of the oligonucleotide or the 3' side of the oligonucleotide.

The oligonucleotide may be any size. Preferably the oligonucleotide has 8 to 100 nucleotides. In other embodiments the oligonucleotide is 8 to 40 nucleotides in length.

In some embodiments $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA. Preferably $X_1X_2$ are GpA or GpT and $X_3X_4$ are TpT. In other preferred embodiments $X_1$ or $X_2$ or both are purines and $X_3$ or $X_4$ or both are pyrimidines or $X_1X_2$ are GpA and $X_3$ or $X_4$ or both are pyrimidines. In one embodiment $X_2$ is a T and $X_3$ is a pyrimidine. The oligonucleotide may be isolated or synthetic.

The invention also includes the use of a non-nucleic acid adjuvant in some aspects. The non-nucleic acid adjuvant in some embodiments is an adjuvant that creates a depo effect, an immune stimulating adjuvant, or an adjuvant that creates a depo effect and stimulates the immune system. Preferably the adjuvant that creates a depo effect is selected from the group consisting of alum (e.g., aluminum hydroxide, aluminum phosphate) emulsion based formulations including mineral oil, non-mineral oil, water-in-oil or oil-in-water emulsions, such as the Seppic ISA series of Montanide adjuvants; MF-59; and PROVAX. In some embodiments the immune stimulating adjuvant is selected from the group consiting of saponins purified from the bark of the Q. saponaria tree, such as QS21; poly[di(carboxylatophenoxy) phosphazene (PCPP) derivatives of lipopolysaccharides such as monophosphorlyl lipid (MPL), muramyl dipeptide (MDP) and threonyl muramyl dipeptide (tMDP); OM-174; and Leishmania elongation factor. In one embodiment the adjuvant that creates a depo effect and stimulates the immune system is selected from the group consiting of ISCOMS; SB-AS2; SB-AS4; non-ionic block copolymers that form micelles such as CRL 1005; and Syntex Adjuvant Formulation.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 12 is a bar graph depicting titers of antibodies against HBsAg (anti-HBs) in millilnternational Units per millilitre (mIU/ml) in orangutans immunized with 10 μg HBsAg with alum (like the HBV commercial vaccine), CpG oligonucleotides (CpG ODN 2006, 1 mg) or both alum and CpG ODN. The numbers above the bars show the number of animals with seroconversion (upper numbers, >1 mIU/ml) or with seroprotection (lower numbers, >10 mIU/ml) over the total number of animals immunized. A titer of 10 mIU/ml is considered sufficient to protect humans and great apes against infection.

DETAILED DESCRIPTION OF THE INVENTION

Figure 1:
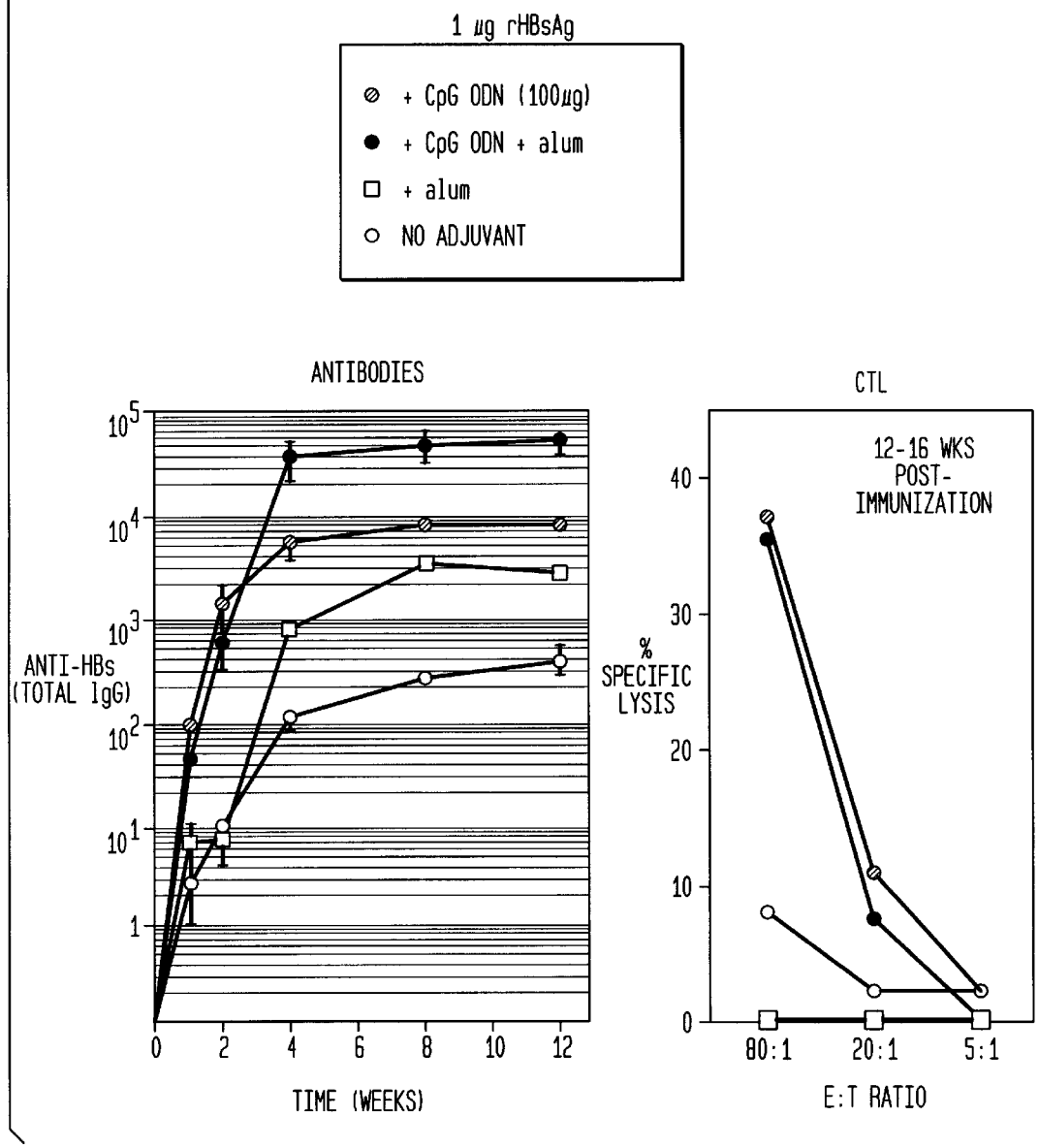
FIG. 1 has two graphs illustrating humoral and cytotoxic T-lymphocyte (CTL) responses in adult BALB/c mice immunized with 1 µg recombinant HBsAg protein alone, adsorbed onto alum (25 mg $Al^{3+}$/mg HBsAg), with 100 µg of immunostimulatory CpG ODN 1826, or with both alum and CpG ODN. Left panel: Each point represents the group mean (n=10) for titers of anti-HBs (total IgG) as determined in triplicate by end-point dilution ELISA assay. End-point titers were defined as the highest plasma dilution that resulted in an absorbance value (OD 450) two times greater than that of control non-immune plasma with a cut-off value of 0.05. Rightpanel: Each point represents the mean % specific lysis at the indicated effector: target (E:T) cell ratio in a chromium release assay with HBsAg-expressing cells as targets.

The invention in one aspect is based on the discovery that formulations containing combinations of immunostimulatory CpG oligonucleotides and non-nucleic acid adjuvants synergistically enhance immune responses to a given antigen. Different non-nucleic acid adjuvants used in combination in the prior art have different affects on immune system activation. Some combinations of adjuvants produce an antigen-specific response that is no better than the best of the individual components and some combinations even produce lower antigen specific responses than with the individual adjuvants used alone. In Gordon et al., for instance, when humans were immunized with C terminal recombinant malaria circumsporozite antigen with alum alone or alum in combination with monophosphoryl lipid A (MPL), the subjects receiving alum alone developed higher antigen specific antibodies at several time points than subjects receiving the combination of adjuvants.

It has been discovered according to the invention that the combination of immunostimulatory CpG oligonucleotides and alum, MPL and other adjuvants results in a synergistic immune response. Compared with the recombinant hepatitis B surface antigen (HBsAg) protein vaccine alone, addition of alum increases the level of antibodies in mice against HBsAg (anti-HBs) about 7-fold whereas addition of CpG ODN increases them 32-fold. When CpG ODN and alum are used together, a 500–1000 times higher level of anti-HBs was observed, indicating a strong synergistic response. Additionally, it was found according to the invention that immunization with HBsAg and alum resulted in a strong Th2-type response with almost all IgG being of the IgG1 isotype. CpG ODN induced a high proportion of IgG2a, indicative of a Th1-type response, even in the presence of alum. Furthermore, it was discovered according to the invention that in very young mice (7 day old), immune responses were induced by HBsAg with alum and CpG ODN but not with alum or CpG ODN alone. The antibodies produced with CpG ODN were predominantly of the IgG2a isotype, indicating a strong Th1-type response. This is remarkable considering the strong Th2 bias of the neonatal immune system and the known difficulty in inducing Th1 responses at such a young age. Th1 responses are preferable in some instances since they are associated with IgG2a antibodies that have better neutralization and opsonization capabilities than Th2-type antibodies. As well, Th1 responses are associated with cytotoxic T lymphocytes (CTL) that can attack and kill virus-infected cells. Indeed, CpG ODN, alone or in combination with alum induced good CTL activity in both adult and neonatal mice. These studies demonstrate that the addition of CpG ODN to protein or DNA vaccines in combination with other adjuvants is a valid new adjuvant approach to improve efficacy.

Thus in one aspect the invention is a method of inducing an antigen specific immune response in a subject. The method includes the step of administering to the subject in order to induce an antigen specific immune response an antigen and a combination of adjuvants, wherein the combination of adjuvants includes at least one oligonucleotide containing at least one unmethylated CpG dinucleotide and at least one non-nucleic acid adjuvant, and wherein the combination of adjuvants is administered in an effective amount for inducing a synergistic adjuvant response.

The synergistic combination of adjuvants is particularly useful as a prophylactic vaccine for the treatment of a subject at risk of developing an infection with an infectious organism or a cancer in which a specific cancer antigen has been identified or an allergy where the allergen is known. The combination of adjuvants can also be given without the antigen or allergen for shorter term protection against infection, allergy or cancer, and in this case repeated doses will allow longer term protection. A "subject at risk" as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or even any subject living in an area that an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject is exposed to the antigen, i.e., during pollen season, then that subject is at risk of exposure to the antigen.

There is a need for a prophylactic vaccine that can induce protective immunity against many infectious pathogens more quickly and with fewer doses than traditional vaccines can provide. For instance, fewer than 20% of healthy individuals attain protective levels of anti-hepatitis B (HB) antibodies (10 mIU/ml) after a single dose of subunit hepatitis B Vaccine (HBV) vaccine and only 60–70% reach this level after two doses. Thus, three doses (usually given at 0, 1 and 6 months) are required to seroconvert >90% of vaccinated individuals. The three dose regime is frequently not completed owing to poor patient compliance, and in endemic areas, protective levels may not be induced quickly enough. The methods of the invention are particularly useful as prophylactic treatments because they induce higher levels of antibodies than can be achieved with traditional vaccines and can be administered as fewer total doses.

Additionally between 5 and 10% of individuals are non-responders or hypo-responders to the subunit HBsAg vaccine. This may be MHC-restricted (Kruskall et al., 1992) and is thought to result from a failure to recognize T-helper epitopes. In certain immunocompromised individuals (e.g., kidney dialysis patients, alcoholics) the rate of non-response can approach 50%. As set forth in the Examples below, alum plus CpG ODN gave higher anti-HBs titers than alum alone in a strain of mice which has MHC-restricted hypo-responsiveness to HBsAg, thought to result in a failure to recognize T-helper epitopes. CpG ODN also overcame non-response in mice genetically incapable of providing T-help owing to an absence of class II MHC. Similar results were obtained in orangutans at risk of becoming infected with hepatitis B. It was found that orangutans are hyporesponders to the classical alum-adjuvanted vaccine with less than 10% achieving seroprotection after 2 doses, but that nearly 100% of animals responded with use of CpG oligonucleotides alone or combined with alum. The synergistic response was evident because antibody titers were much higher with CpG ODN plus alum than with CpG ODN alone or alum alone and were more than additive. These results support the proposition that CpG ODN drives the T cell independent activation of B cells. Thus in addition to providing a more effective and easier vaccination protocol the synergistic combination of adjuvants can be used to reduce the percentage of non-responders and hypo-responders.

A subject at risk of developing a cancer is one who is who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and an adjuvant and a CpG oligonucleotide the subject may be able to kill of the cancer cells as they develop. If a tumor begins to form in the subject, the subject will develop a specific immune response against the tumor antigen.

In addition to the use of the combination of adjuvants for prophylactic treatment, the invention also encompasses the use of the combination for the immunotherapeutic treatment of a subject having an infection, an allergy or a cancer. A "subject having an infection" is a subject that has been exposed to an infectious pathogen and has acute or chronic detectable levels of the pathogen in the body. The combination of adjuvants can be used with an antigen to mount an antigen specific immune response that is capable of reducing the level of or eradicating the infectious pathogen. An infectious disease, as used herein, is a disease arising from the presence of a foreign microorganism in the body.

Many types of infectious pathogens do not have any effective treatments and chronic presence of the pathogen can result in significant damage. For instance, the HBV virus is itself non-pathogenic but with chronic infection the partially developed immune response causes inflammatory changes that eventually leads to cirrhosis and increased risk of hepatocellular carcinoma. An estimated one million people die each year from HBV-related liver disease. Persistent HBV infection of the liver results when acute infection fails to launch an appropriate immune response to clear the virus. Such chronic carriers have circulating HBsAg "e" soluble form of the HBV core antigen (HBeAg) without specific immunity. It is thought that the absence of HBV-specific T-cells, including CTL may contribute to the establishment and maintenance of the chronic carrier state. Indeed, many previously infected individuals, even years after clinical and serological recovery, have traces of HBV in their blood and HBV-specific CTL that express activation markers indicative of recent contact with antigen (Rehermann et al., 1996). These results suggest that sterilizing immunity may not occur after HBV infection and that chronic activation of HBV-specific CD4+ and CD8+ T-cells is responsible for keeping the virus under control.

There is currently no cure for the HBV chronic infection. Interferon is used currently but this cures only 10–20% of treated individuals (Niederau et al., 1996). Anti-viral drugs (e.g., lamivudine) can reduce circulating virus to undetectable levels, however these return to pretreatment levels if the drug is stopped. Each of these types of treatment is also expensive and has certain undesirable side-effects. Thus the synergistic combination of adjuvants which induces potent Th1 responses, including CTL, is useful for treating a subject having an infection such as HBV.

A "subject having an allergy" is a subject that has or is at risk of developing an allergic reaction in response to an allergen. An "allergy" refers to acquired hypersensitivity to a substance (allergen). Allergic conditions include but are not limited to eczema, allergic rhinitis or coryza, conjunctivitis, hay fever, bronchial asthma, urticaria (hives) and food allergies, and other atopic conditions.

Currently, allergic diseases are generally treated either symptomatically with antihistimines for example or immunotherapeutically by the injection of small doses of antigen followed by subsequent increasing dosage of antigen. Symptomatic treatment offers only temporary relief. Immunotherapy is believed to induce tolerance to the allergen to prevent further allergic reactions. This approach, however, takes several years to be effective and is associated with the risk of side effects such as anaphylactic response. The methods of the invention avoid these problems.

Allergies are generally caused by IgE antibody generation against harmless allergens. The cytokines that are induced by unmethylated CpG oligonucleotides are predominantly of a class called "Th1" which includes IL-12 and IFN-γ. In contrast, Th2 immune response are associated with the production of IL-4, IL-5 and IL-10. Th1responses include both cell-mediated responses (including cytotoxic T-cells) and antibodies, whereas Th2 responses are associated only with antibodies. The antibodies with a Th1 response are of isotypes (e.g. IgG2a) that have better neutralizing and opsonizing capabilities than those of Th2 isotypes (e.g. IgE that mediates allergic responses). In general, it appears that allergic diseases are mediated by Th2 type immune responses and protective immune responses by Th1 immune response although exaggerated Th1 responses may be also associated with autoimmune diseases.

Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. "Asthma" refers to a disorder of the respiratory system characterized by inflammation, narrowing of the airways and increased reactivity of the airways to inhaled agents. Asthma is frequently, although not exclusively associated with atopic or allergic symptoms.

Based on the ability of the CpG oligonucleotides to shift the immune response in a subject from a Th2 (which is associated with production of IgE antibodies and allergy) to a Th1 response (which is protective against allergic reactions), an effective dose of a CpG oligonucleotide can be administered to a subject to treat or prevent an allergy.

Since Th1 responses are even more potent with CpG DNA combined with non-nucleic acid adjuvants, the combination of adjuvants of the present invention will have significant therapeutic utility in the treatment of allergic conditions such as asthma. Such combinations of adjuvants could be used alone or in combination with allergens.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A "subject" shall mean a human or vertebrate animal including but not limited to a dog, cat, horse, cow, pig, sheep, goat, chicken, primate, (e.g., monkey), fish (aquaculture species e.g. salmon, trout and other salmonids), rat, and mouse.

The subject is administered a combination of adjuvants, wherein the combination of adjuvants includes at least one oligonucleotide containing at least one unmethylated CpG dinucleotide and at least one non-nucleic acid adjuvant. An oligonucleotide containing at least one unmethylated CpG dinucleotide is a nucleic acid molecule which contains an unmethylated cytosine-guanine dinucleotide sequence (i.e. "CpG DNA" or DNA containing a 5' cytosine followed by 3' guanosine and linked by a phosphate bond) and activates the immune system. The CpG oligonucleotides can be double-stranded or single-stranded. Generally, double-stranded molecules are more stable in vivo, while single-stranded molecules have increased immune activity. The CpG oligonucleotides or combination of adjuvants can be used with or without antigen.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g. genomic or cDNA), but are preferably synthetic (e.g. produced by oligonucleotide synthesis). The entire CpG oligonucleotide can be unmethylated or portions may be unmethylated but at least the C of the 5' CG 3' must be unmethylated.

In one preferred embodiment the invention provides a CpG oligonucleotide represented by at least the formula:

$$5'N_1X_1CGX_2N_23'$$

wherein at least one nucleotide separates consecutive CpGs; $X_1$ is adenine, guanine, or thymine; $X_2$ is cytosine, adenine, or thymine; N is any nucleotide and $N_1$ and $N_2$ are nucleic acid sequences composed of from about 0–25 N's each.

In another embodiment the invention provides an isolated CpG oligonucleotide represented by at least the formula:

$$5'N_1X_1X_2CGX_3X_4N_23'$$

wherein at least one nucleotide separates consecutive CpGs; $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, CpT, ApT, TpG, ApG, CpG, TpC, ApC, CpC, TpA, ApA, and CpA; N is any nucleotide and $N_1$ and $N_2$ are nucleic acid sequences composed of from about 0–25 N's each. Preferably $X_1X_2$ are GpA or GpT and $X_3X_4$ are TpT. In other preferred embodiments $X_1$ or $X_2$ or both are purines and $X_3$ or $X_4$ or both are pyrimidines or $X_1X_2$ are GpA and $X_3$ or $X_4$ or both are pyrimidines. In a preferred embodiment $N_1$ and $N_2$ of the nucleic acid do not contain a CCGG or CGCG quadmer or more than one CCG or CGG trimer. The effect of a a CCGG or CGCG quadmer or more than one CCG or CGG trimer depends in part on the status of the oligonucleotide backbone. For instance, if the oligonucleotide has a phosphodiester backbone or a chimeric backbone the inclusion of these sequences in the oligonucleotide will only have minimal if any affect on the biological activity of the oligonucleotide. If the backbone is completely phosphorothioate or significantly phosphorothioate then the inclusion of these sequences may have more influence on the biological activity or the kinetics of the biological activity. In another preferred embodiment the CpG oligonucleotide has the sequence $5'TCN_1TX_1X_2CGX_3X_43'$.

Preferably the CpG oligonucleotides of the invention include $X_1X_2$ selected from the group consisting of GpT, GpG, GpA and ApA and $X_3X_4$ is selected from the group consisting of TpT, CpT and GpT. For facilitating uptake into cells, CpG containing oligonucleotides are preferably in the range of 8 to 30 bases in length. However, nucleic acids of any size greater than 8 nucleotides (even many kb long) are capable of inducing an immune response according to the invention if sufficient immunostimulatory motifs are present, since larger nucleic acids are degraded into oligonucleotides inside of cells. Preferred synthetic oligonucleotides do not include a CCGG or CGCG quadmer or more than one CCG or CGG trimer at or near the 5' and/or 3' terminals. Stabilized oligonucleotides, where the oligonucleotide incorporates a phosphate backbone modification, as discussed in more detail below are also preferred. The modification may be, for example, a phosphorothioate or phosphorodithioate modification. Preferably, the phosphate backbone modification occurs at the 5' end of the nucleic acid for example, at the first two nucleotides of the 5' end of the oligonucleotide. Further, the phosphate backbone modification may occur at the 3' end of the nucleic acid for example, at the last five nucleotides of the 3' end of the nucleic acid. Alternatively the oligonucleotide may be completely or partially modified.

Preferably the CpG oligonucleotide is in the range of between 8 and 100 and more preferably between 8 and 30 nucleotides in size. Alternatively, CpG oligonucleotides can be produced on a large scale in plasmids. These may be administered in plasmid form or alternatively they can be degraded into oligonucleotides.

The CpG oligonucleotide and immunopotentiating cytokine may be directly administered to the subject or may be administered in conjunction with a nucleic acid delivery complex. A "nucleic acid/cytokine delivery complex" shall mean a nucleic acid molecule and/or cytokine associated with (e.g. ionically or covalently bound to; or encapsulated within) a targeting means (e.g. a molecule that results in higher affinity binding to target cell (e.g. dendritic cell surfaces and/or increased cellular uptake by target cells). Examples of nucleic acid/cytokine delivery complexes include nucleic acids/cytokines associated with: a sterol (e.g. cholesterol), a lipid (e.g. a cationic lipid, virosome or liposome), or a target cell specific binding agent (e.g. a ligand recognized by target cell specific receptor). Preferred complexes should be sufficiently stable in vivo to prevent significant uncoupling prior to internalization by the target cell. However, the complex should be cleavable under appropriate conditions within the cell so that the nucleic acid/cytokine is released in a functional form.

"Palindromic sequence" shall mean an inverted repeat (i.e. a sequence such as ABCDEE'D'C'B'A' in which A and A' are bases capable of forming the usual Watson-Crick base pairs. In vivo, such sequences may form double-stranded structures. In one embodiment the CpG oligonucleotide contains a palindromic sequence. A palindromic sequence used in this context refers to a palindrome in which the CpG is part of the palindrome, and preferably is the center of the palindrome. In another embodiment the CpG oligonucleotide is free of a palindrome. A CpG oligonucleotide that is free of a palindrome is one in which the CpG dinucleotide is not part of a palindrome. Such an oligonucleotide may include a palindrome in which the CpG is not part of the palindrome.

A "stabilized nucleic acid molecule" shall mean a nucleic acid molecule that is relatively resistant to in vivo degradation (e.g. via an exo- or endo-nuclease). Stabilization can be a function of length or secondary structure. Unmethylated CpG oligonucleotides that are tens to hundreds of kbs long are relatively resistant to in vivo degradation, particularly when in a double-stranded closed-circular form (i.e., a plamid). For shorter CpG oligonucleotides, secondary structure can stabilize and increase their effect. For example, if the 3' end of an oligonucleotide has self-complementarity to an upstream region, so that it can fold back and form a sort of stem loop structure, then the oligonucleotide becomes stabilized and therefore exhibits more activity.

Preferred stabilized oligonucleotides of the instant invention have a modified backbone. It has been demonstrated that modification of the oligonucleotide backbone provides enhanced activity of the CpG oligonucleotides when administered in vivo. CpG constructs, including at least two phosphorothioate linkages at the 5' end of the oligonucleotide in multiple phosphorothioate linkages at the 3' end, preferably 5, provides maximal activity and protected the oligonucleotide from degradation by intracellular exo- and endo-nucleases. Other modified oligonucleotides include phosphodiester modified oligonucleotide, combinations of phosphodiester and phosphorothioate oligonucleotide, methylphosphonate, methylphosphorothioate, phosphorodithioate, and combinations thereof. Each of these combinations and their particular effects on immune cells is discussed in more detail in copending PCT Published Patent Applications claiming priority to U.S. Ser. Nos. 08/738,652 and 08/960,774, filed on Oct. 30, 1996 and Oct. 30, 1997 respectively, the entire contents of which is hereby incorporated by reference. It is believed that these modified oligonucleotides may show more stimulatory activity due to enhanced nuclease resistance, increased cellular uptake, increased protein binding, and/or altered intracellular localization.

Both phosphorothioate and phosphodiester oligonucleotides containing CpG motifs are active in immune cells. However, based on the concentration needed to induce CpG specific effects, the nuclease resistant phosphorothioate backbone CpG oligonucleotides are more potent (2 µg/ml for the phosphorothioate vs. a total of 90 µg/ml for phosphodiester).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

The nucleic acid sequences of the invention which are useful as adjuvants are those broadly described above and disclosed in PCT Published Patent Applications claiming priority to U.S. Ser. Nos. 08/738,652 and 08/960,774, filed on Oct. 30, 1996 and Oct. 30, 1997 respectively. Exemplary sequences include but are not limited to those immunostimulatory sequences shown in Table 1.

The stimulation index of a particular immunostimulatory CpG DNA can be tested in various immune cell assays. Preferably, the stimulation index of the CpG oligonucleotide with regard to B cell proliferation is at least about 5, preferably at least about 10, more preferably at least about 15 and most preferably at least about 20 as determined by incorporation of $^3$H uridine in a murine B cell culture, which has been contacted with 20 µM of oligonucleotide for 20 h at 37° C. and has been pulsed with 1 µCi of $^3$H uridine; and harvested and counted 4 h later as described in detail in copending PCT Published Patent Applications claiming priority to U.S. Ser. Nos. 08/38,652 and 08/960,774, filed on Oct. 30, 1996 and Oct. 30, 1997 respectively. For use in vivo, for example, it is important that the CpG oligonucleotide and adjuvant be capable of effectively inducing activation of Ig expressing B cells. Oligonucleotides which can accomplish this include, for example, but are not limited to those oligonucleotides described in PCT Published Patent Applications claiming priority to U.S. Ser. Nos. 08/738,652 and 08/960,774, filed on Oct. 30, 1996 and Oct. 30, 1997 respectively.

The oligonucleotide containing at least one unmethylated CpG is used in combination with a non-nucleic acid adjuvant and an antigen to activate the immune response. A "non-nucleic acid adjuvant" is any molecule or compound except for the CpG oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system. In infants, the oligonucleotide containing at least one unmethylated CpG is used alone or in combination with a non-nucleic acid adjuvant and an antigen to activate a cellular immune response.

An "adjuvant that creates a depo effect" as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An "immune stimulating adjuvant" is an adjuvant that causes activation of a cell of the immune system. It may, for instance, cause an immune cell to produce and secrete cytokines. This class of adjuvants includes but is not limited to saponins purified from the bark of the Q. saponaria tree, such as QS21 (a glycolipid that elutes in the $21^{st}$ peak with HPLC fractionation; Aquila Biopharmaceuticals, Inc., Worcester, Mass.); poly[di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

"Adjuvants that create a depo effect and stimulate the immune system" are those compounds which have both of the above-identified functions. This class of adjuvants includes but is not limited to ISCOMS Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

When the CpG oligonucleotide containing at least one unmethylated CpG is administered in conjunction with another adjuvant, the CpG oligonucleotide can be administered before, after, and/or simultaneously with the other adjuvant. For instance, the combination of adjuvants may be administered with a priming dose of antigen. Either or both of the adjuvants may then be administered with the boost dose. Alternatively, the combination of adjuvants may be administered with a boost dose of antigen. Either or both of the adjuvants may then be administered with the prime dose. A "prime dose" is the first dose of antigen administered to the subject. In the case of a subject that has an infection the prime dose may be the initial exposure of the subject to the infectious microbe and thus the combination of adjuvants is administered to the subject with the boost dose. A "boost dose" is a second or third, etc, dose of antigen administered to a subject that has already been exposed to the antigen. In some cases the prime dose administered with the combination of adjuvants is so effective that a boost dose is not required to protect a subject at risk of infection from being infected. In cases where the combination of adjuvants is given without antigen, with repeated administrations, CpG oligonucleotides or one of the components in the combination may be given alone for one or more of the administrations.

The CpG oligonucleotide containing at least one unmethylated CpG can have an additional efficacy (e.g., antisense) in addition to its ability to enhance antigen-specific immune responses.

An "antigen" as used herein is a molecule capable of provoking an immune response. Antigens include but are not limited to peptides, polypeptides, cells, cell extracts, polysaccharides, polysaccharide conjugates, lipids, glycoliopids and carbohydrates. Antigens may be given in a crude, purified or recombinant form and polypeptide/peptide antigens, including peptide mimics of polysaccharides, may also be encoded within nucleic. The term antigen broadly includes any type of molecule which is recognized by a host immune system as being foreign. Antigens include but are not limited to cancer antigens, microbial antigens, and allergens.

A "cancer antigen" as used herein is a compound, such as a peptide, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research*, 54:1055, by partially purifying the antigens, by recombinant technology, or by de novo synthesis of known antigens. Cancer antigens include antigens that are recombinately an immunogenic portion of or a whole tumor or cancer. Such antigens can be isolated or prepared recombinatly or by any other means known in the art.

A "microbial antigen" as used herein is an antigen of a microorganism and includes but is not limited to infectious virus, infectious bacteria, infectious parasites and infectious fingi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Most such antigens are used routinely in the art and are well known to those of ordinary skill in the art. Another example is a peptide mimic of a polysaccharide antigen.

Examples of infectious virus that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to Pasteurella species, Staphylococci species, and Streptococcus species. Gram negative bacteria include, but are not limited to, *Escherichia coli*, Pseudomonas species, and Salmonella species. Specific examples of infectious bacteria include but are not limited to: Helicobacterpyloris, Borelia burgdorferi, Legionella pneumophilia, Mycobacteria sps (e.g. M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes (Group A Streptococcus), *Streptococcus agalactiae* (Group B Streptococcus), Streptococcus (viridans group), *Streptococcusfaecalis, Streptococcus bovis*, Streptococcus (*anaerobic* sps.), *Streptococcus pneumoniae*, pathogenic Campylobacter sp., Enterococcus sp., *Haemophilus infuenzae, Bacillus antracis*, corynebacterium diphtheriae, corynebacterium sp., Erysipelothrix rhusiopathiae, Clostridium perfringers, Clostridium tetani, Enterobacter aerogenes, *Klebsiella pneumoniae, Pasturella multocida*, Bacteroides sp., *Fusobacterium nucleatum, Streptobacillus moniliformis, Treponema pallidium, Treponema pertenue, Leptospira, Rickettsia*, and *Actinomyces israelli*.

Examples of infectious fingi include: *Cryptococcus neoformans, Histoplasma capsulatum, Coccidioides immitis, Blastomyces dermatitidis, Chlamydia trachomatis, Candida albicans*. Examples of infectious parasites include Plasmodium such as *Plasmodium falciparum, Plasmodium malariae, Plasmodium ovale*, and *Plasmodium vivax*. Other infectious organisms (i.e. protists) include Toxoplasma gondii.

Other medically relevant microorganisms have been descried extensively in the literature, e.g., see C. G. A Thomas, *Medical Microbiology*, Bailliere Tindall, Great Britain 1983, the entire contents of which is hereby incorporated by reference.

Although many of the microbial antigens described above relate to human disorders, the invention is also useful for treating other nonhuman vertebrates. Nonhuman vertebrates are also capable of developing infections which can be prevented or treated with the synergistic combination of adjuvants disclosed herein. For instance, in addition to the treatment of infectious human diseases, the methods of the invention are useful for treating infections of animals.

As used herein, the term "treat","treated", or "treating" when used with respect to an infectious disease refers to a prophylactic treatment which increases the resistance of a subject (a subject at risk of infection) to infection with a pathogen or, in other words, decreases the likelihood that the subject will become infected with the pathogen, as well as a treatment after the subject (a subject who has been infected) has become infected in order to fight the infection, e.g., reduce or eliminate the infection or prevent it from becoming worse. Many vaccines for the treatment of non-human vertebrates are disclosed in Bennett, K. *Compendium of Veterinary Products*, 3rd ed. North American Compendiums, Inc., 1995. As discussed above, antigens include infectious microbes such as virus, bacteria, parasites and fungi and fragments thereof, derived from natural sources or synthetically. Infectious virus of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesvirises (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting.

In addition to the use of the combination of CpG oligonucleotides and non-nucleic acid adjuvants to induce an antigen specific immune response in humans, the methods of the preferred embodiments are particularly well suited for treatment of birds such as hens, chickens, turkeys, ducks, geese, quail, and pheasant. Birds are prime targets for many types of infections.

Hatching birds are exposed to pathogenic microorganisms shortly after birth. Although these birds are initially protected against pathogens by maternal derived antibodies, this protection is only temporary, and the bird's own immature immune system must begin to protect the bird against the pathogens. It is often desirable to prevent infection in young birds when they are most susceptible. It is also desirable to prevent against infection in older birds, especially when the birds are housed in closed quarters, leading to the rapid spread of disease. Thus, it is desirable to administer the CpG oligonucleotide and the non-nucleic acid adjuvant of the invention to birds to enhance an antigen-specific immune response when antigen is present. The CpG oligonucleotide and the non-nucleic acid adjuvant of the invention could also be administered to birds without antigen to protect against infection of a wide variety of pathogens.

An example of a common infection in chickens is chicken infectious anemia virus (CIAV). CIAV was first isolated in Japan in 1979 during an investigation of a Marek's disease vaccination break (Yuasa et al., 1979, Avian Dis. 23:366–385). Since that time, CIAV has been detected in commercial poultry in all major poultry producing countries (van Bulow et al., 1991, pp.690–699) in Diseases of Poultry, 9th edition, Iowa State University Press).

CIAV infection results in a clinical disease, characterized by anemia, hemorrhage and immunosuppression, in young susceptible chickens. Atrophy of the thymus and of the bone marrow and consistent lesions of CIAV-infected chickens are also characteristic of CIAV infection. Lymphocyte depletion in the thymus, and occasionally in the bursa of Fabricius, results in immunosuppression and increased susceptibility to secondary viral, bacterial, or fungal infections which then complicate the course of the disease. The immunosuppression may cause aggravated disease after infection with one or more of Marek's disease virus (MDV), infectious bursal disease virus, reticuloendotheliosis virus, adenovirus, or reovirus. It has been reported that pathogenesis of MDV is enhanced by CIAV (DeBoer et al., 1989, p. 28 In Proceedings of the 38th Western Poultry Diseases Conference, Tempe, Ariz.). Further, it has been reported that CIAV aggravates the signs of infectious bursal disease (Rosenberger et al., 1989, Avian Dis. 33:707–713). Chickens develop an age resistance to experimentally induced disease due to CAA. This is essentially complete by the age of 2 weeks, but older birds are still susceptible to infection (Yuasa, N. et al., 1979 supra; Yuasa, N. et al., Arian Diseases 24, 202–209, 1980). However, if chickens are dually infected with CAA and an immunosuppressive agent (IBDV, MDV etc.) age resistance against the disease is delayed (Yuasa, N. et al., 1979 and 1980 supra; Bulow von V. et al., J. Veterinary Medicine 33, 93–116, 1986). Characteristics of CIAV that may potentiate disease transmission include high resistance to environmental inactivation and some common disinfectants. The economic impact of CIAV infection on the poultry industry is clear from the fact that 10% to 30% of infected birds in disease outbreaks die.

Vaccination of birds, like other vertebrate animals can be performed at any age. Normally, vaccinations are performed at up to 12 weeks of age for a live microorganism and between 14–18 weeks for an inactivated microorganism or other type of vaccine. For in ovo vaccination, vaccination can be performed in the last quarter of embryo development. The vaccine may be administered subcutaneously, by spray, orally, intraocularly, intratracheally, nasally, in ovo or by other methods described herein. Thus, the CpG oligonucleotide and non-nucleic acid adjuvant of the invention can be administered to birds and other non-human vertebrates using routine vaccination schedules and the antigen is administered after an appropriate time period as described herein.

Cattle and livestock are also susceptible to infection. Disease which affect these animals can produce severe economic losses, especially amongst cattle. The methods of the invention can be used to protect against infection in livestock, such as cows, horses, pigs, sheep, and goats. The CpG oligonucleotide and the non-nucleic acid adjuvant of the invention could also be administered with antigen for antigen-specific protection of long duration or without antigen for short term protection against a wide variety of diseases, including shipping fever.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the pestivirus genus. Although, Pestiviruses were previously classified in the Togaviridae family, some studies have suggested their reclassification within the Flaviviridae family along with the flavivirus and hepatitis C virus (HCV) groups (Francki, et al., 1991).

BVDV, which is an important pathogen of cattle can be distinguished, based on cell culture analysis, into cytopathogenic (CP) and noncytopathogenic (NCP) biotypes. The NCP biotype is more widespread although both biotypes can be found in cattle. If a pregnant cow becomes infected with an NCP strain, the cow can give birth to a persistently infected and specifically immunotolerant calf that will spread virus during its lifetime. The persistently infected cattle can succumb to mucosal disease and both biotypes can then be isolated from the animal. Clinical Manifestations can include abortion, teratogenesis, and respiratory problems, mucosal disease and mild diarrhea. In addition, severe thrombocytopenia, associated with herd epidemics, that may result in the death of the animal has been described and strains associated with this disease seem more virulent than the classical BVDVs.

Equine herpesviruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Primary infection of upper respiratory tract of young horses results in a febrile illness which lasts for 8 to 10 days. Immunologically experienced mares may be reinfected via the respiratory tract without disease becoming apparent, so that abortion usually occurs without warning. The neurological syndrome is associated with respiratory disease or abortion and can affect animals of either sex at any age, leading to incoordination, weakness and posterior paralysis (Telford, E. A. R. et al., Virology 189, 304–316, 1992). Other EHV's include EHV-2, or equine cytomegalovirus, EHV-3, equine coital exanthema virus, and EHV-4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al. (1990) Lancet 36:1538–1541; Desrosiers et al. PNAS USA (1989) 86:6353–6357; Murphey-Corb et al. (1989) Science 246:1293–1297; and Carlson et al. (1990) AIDS Res. Human Retroviruses 6:1239–1246). A recombinant HIV gp120 vaccine has been reported to afford protection in chimpanzees (Berman et al. (1990) Nature 345:622–625).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to prevent them against infection.

Domestic cats may become infected with several retroviruses, including but not limited to feline leukemia virus (FeLV), feline sarcoma virus (FeSV), endogenous type C oncornavirus (RD-114), and feline syncytia-forming virus (FeSFV). Of these, FeLV is the most significant pathogen, causing diverse symptoms, including lymphoreticular and myeloid neoplasms, anemias, immune mediated disorders, and an immunodeficiency syndrome which is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (also referred to as feline immunodeficiency) was first reported in Pedersen et al. (1987) Science 235:790–793. Characteristics of FIV have been reported in Yamamoto et al. (1988) Leukemia, December Supplement 2:204S–215S; Yamamoto et al. (1988) Am. J. Vet. Res. 49:1246–1258; and Ackley et al. (1990) J. Virol. 64:5652–5655. Cloning and sequence analysis of FIV have been reported in Olmsted et al. (1989) Proc. Natl. Acad. Sci. USA 86:2448–2452 and 86:4355–4360.

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old.

Viral, bacterial and parasitic diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Fish are currently protected against a variety of bacterial infections with whole killed vaccines with oli adjuvants, but there is only one licensed vaccine for fish against a viral disease. Nucleic acid based vaccinations are described in U.S. Pat. No. 5,780,448 issued to Davis and these have been shown to be protective against at least two different viral diseases.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered orally or by immersion or injection.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

Polypeptides of viral aquaculture pathogens include but are not limited to glycoprotein (G) or nucleoprotein (N) of viral hemorrhagic septicemia virus (VHSV); G or N proteins of infectious hematopoietic necrosis virus (IHNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Polypeptides of bacterial pathogens include but are not limited to an iron-regulated outer membrane protein, (IROMP), an outer membrane protein (OMP), and an A-protein of Aeromonis salmonicida which causes furunculosis, p57 protein of Renibacterium salmoninarum which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (IROMP), and a structural protein of Pasteurellosis; an OMP and a flagellar protein of Vibrosis anguillarum and V. ordalii; a flagellar protein, an OMP protein,aroA, and purA of Edwardsiellosis ictaluri and E. tarda; and surface antigen of Ichthyophthirius; and a structural and regulatory protein of Cytophaga columnari; and a structural and regulatory protein of Rickettsia.

Polypeptides of a parasitic pathogen include but are not limited to the surface antigens of Ichthyophthirius.

An "allergen" refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); Dermatophagoides (e.g. *Dermatophagoides farinae*); Felis (*Felis domesticus*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alder; Alnus (*Alnus gultinoasa*); Betula (*Betula verrucosa*); Quercus (*Quercus alba*); Olea (Olea europa); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *PArrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

In some aspects of the invention the antigen is a polypeptide. Minor modifications of the primary amino acid sequences of polypeptide antigens may also result in a polypeptide which has substantially equivalent antigenic activity as compared to the unmodified counterpart polypeptide. Such modifications may be deliberate, as by site-directed mutagenesis, or may be spontaneous. All of the polypeptides produced by these modifications are included herein as long as antigenicity still exists. The polypeptide may be, for example, a viral polypeptide. One non-limiting example of an antigen useful according to the invention is the hepatitis B surface antigen. Experiments using this antigen are described in the Examples below.

The term "substantially purified" as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis.

The invention also utilizes polynucleotides encoding the antigenic polypeptides. It is envisioned that the antigen may be delivered to the subject in a nucleic acid molecule which encodes for the antigen such that the antigen must be expressed in vivo. The nucleic acid encoding the antigen is operatively linked to a gene expression sequence which directs the expression of the antigen nucleic acid within a eukaryotic cell. The "gene expression sequence" is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter, muscle creatine kinase promoter, human elongation factor promoter and other constitutive promoters. Exemplary viral promoters which function constitutively in eukaryotic cells include, for example, promoters from the simian virus (e.g., SV40), papilloma virus, adenovirus, human immunodeficiency virus (HIV), rous sarcoma virus, cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

The antigen nucleic acid is operatively linked to the gene expression sequence. As used herein, the antigen nucleic acid sequence and the gene expression sequence are said to be "operably linked" when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the antigen sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a gene expression sequence would be operably linked to an antigen nucleic acid sequence if the gene expression sequence were capable of effecting transcription of that antigen nucleic acid sequence such that the resulting transcript is translated into the desired protein or polypeptide.

The antigen nucleic acid sequence may encode a protein, polypeptide, peptide, or peptide mimic of a polysaccharide. It may also encode more than one antigenic component as a fusion construct. More than one antigen-encoding sequence may be included in the same plasmid vector and these may be linked to the same or different gene expression sequences.

The antigen nucleic acid of the invention may be delivered to the immune system alone or in association with a vector. In its broadest sense, a "vector" is any vehicle capable of facilitating the transfer of the antigen nucleic acid to the cells of the immune system and preferably APCs so that the antigen can be expressed and presented on the surface of an APC. Preferably, the vector transports the nucleic acid to the immune cells with reduced degradation relative to the extent of degradation that would result in the absence of the vector. The vector optionally includes the above-described gene expression sequence to enhance expression of the antigen nucleic acid in APCs. In general, the vectors useful in the invention include, but are not limited to, plasmids, phagemids, viruses, other vehicles derived from viral or bacterial sources that have been manipulated by the insertion or incorporation of the antigen nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991).

Preferred virus for certain applications are the adeno-virus and adeno-associated virus which are double-stranded DNA viruses that have already been approved for human use in gene therapy and immunotherapy trials. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See e.g., Sanbrook et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and ligation reactions to remove and add specific fragments of DNA. Plasmids such as those used for DNA vaccines may be delivered by a variety of parenteral, mucosal and topical routes. For example the plasmid DNA can be injected by intramuscular, intradermal, subcutaneous or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

It has recently been discovered that gene carrying plasmids can be delivered to the immune system using bacteria. Modified forms of bacteria such as Salmonella can be transfected with the plasmid and used as delivery vehicles. The bacterial delivery vehicles can be administered to a host subject orally or by other administration means. The bacteria deliver the plasmid to immune cells, e.g. dendritic cells, probably by passing through the gut barrier. High levels of immune protection have been established using this methodology.

In other aspects the invention includes a method for immunizing an infant by administering to an infant an antigen and an oligonucleotide containing at least one unmethylated CpG dinucleotide in an effective amount for inducing cell mediated immunity in the infant. In some embodiments the infant is also administered at least one non-nucleic acid adjuvant, as described above. Cell mediated immunity, as used herein, refers to an immune response which involves an antigen specific T cell reaction. The presence of cell mediated immunity can be determined directly by the induction of Th1 cytokines (e.g., IFN-γ, IL-12) and antigen-specific cytotoxic T-cell lymphocytes (CTL). The presence of cell mediated immunity is also indicated indirectly by the isotype of antigen-specific antibodies that are induced (e.g. IgG2a>>IgG1 in mice). Thus, if Th1 cytokines or CTL or TH2-like antibodies are induced, cell mediated immunity is induced according to the invention. As discussed above, Th1 cytokines include but are not limited to IL-12 and IFN-γ.

Neonates (newborn) and infants (which include humans three months of age and referred to hereinafter as infants) born in HBV endemic areas require particularly rapid induction of strong HBV-specific immunity owing to the high rate of chronicity resulting from infection at a young age. Without immunoprophylaxis, 70–90% of infants born to mothers positive for both HBsAg and the "e" antigen (HBeAg) become infected and almost all of these become chronic carriers (Stevens et al., 1987). Even when vaccinated with a four dose regime of the HBV subunit vaccine commencing on the day of birth, 20% of such infants became chronically infected and this was reduced to only 15% if they were also given HBV-specific immunoglobulin (Chen et al. 1996) HBV chronicity results in 10–15% of individuals infected as adolescents or adults, but 90–95% for those infected (either vertically or horizontally) as infants. CpG oligonucleotides may be used, according to the invention, to reduce this further owing to a more rapid appearance and higher titers of anti-HBs antibodies and the induction of HBV-specific CTL, which could help clear virus from the liver of babies infected in utero, and which likely account for most of the failures with infant vaccination.

The invention further provides a method of modulating the level of a cytokine. The term "modulate" envisions the suppression of expression of a particular cytokine when lower levels are desired, or augmentation of the expression of a particular cytokine when higher levels are desired. Modulation of a particular cytokine can occur locally or systemically. CpG oligonucleotides can directly activate macrophages and dendritic cells to secrete cytokines. No direct activation of proliferation or cytokine secretion by highly purified T cells has been found, although they are induced to secrete cytokines by cytokines secreted from macrophages and may be costimulated through the T cell Receptor. Cytokine profiles determine T cell regulatory and effector functions in immune responses. In general, Th1-type cytokines are induced, thus the immunostimulatory nucleic acids promote a Th1 type antigen-specific immune response including cytotoxic T-cells.

Cytokines also play a role in directing the T cell response. Helper (CD4$^+$) T cells orchestrate the immune response of mammals through production of soluble factors that act on other immune system cells, including B and other T cells. Most mature CD4$^+$ T helper cells express one of two cytokine profiles: Th1 or Th2. Th1 cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. The Th1 subset promotes both cell-mediated immunity, and humoral immunity that is characterized by immunoglobulin class switching to IgG$_{2a}$ in mice. Th1 responses may also be associated with delayed-type hypersensitivity and autoimmune disease. The Th2 subset induces primarily humoral immunity and induce class switching to IgG$_1$, and IgE. The antibody isotypes associated with Th1 responses generally have good neutralizing and opsonizing capabilities whereas those associated with Th2 responses are associated more with allergic responses.

Several factors have been shown to influence commitment to Th1 or Th2 profiles. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear to be required for the establishment of the Th2 cytokine profile and to down-regulate Th1 cytokine production; the effects of IL4 are in some cases dominant over those of IL-12. IL-13 was shown to inhibit expression of inflammatory cytokines, including IL-12 and TNF-α by LPS-induced monocytes, in a way similar to IL-4. The IL-12 p40 homodimer binds to the IL-12 receptor and may antagonizes IL-12 biological activity; thus it blocks the pro-Th1 effects of IL-12 in some animals.

In other aspects the invention includes a method of inducing a Th1 immune response in a subject by administering to the subject a combination of adjuvants in an effective amount for inducing a Th1 immune response. The combination of adjuvants includes at least one oligonucleotide containing at least one umnethylated CpG dinucleotide and at least one non-nucleic acid adjuvant. It was not previously known that when CpG was combined with a non-nucleic acid adjuvant, as described above, that the combination would produce an immune response with a Th1 profile to an extent that the individual adjuvants could not produce alone. Preferably the extent of the Th profile produced by the combination of adjuvants is synergistic. Another aspect of the invention is to induce a Th response by using CPG with a non-nucleic acid adjuvant that by itself induces a Th2 response.

As described above a Th2 profile is characterized by production of IL-4 and IL-10. Non-nucleic acid adjuvants that induce Th2 or weak Th1 responses include but are not limited to alum, saponins, oil-in-water and other emulsion formulations and SB-As4. Adjuvants that induce Th1 responses include but are not limited to MPL, MDP, ISCOMS, IL-12, IFN-γ, and SB-AS2. When the CpG oligonucleotide is administered with a non-nucleic acid adjuvant the combination of adjuvants causes a commitment to a Th1 profile, that neither the adjuvant nor the CpG oligonucleotide is capable of producing on its own. Furthermore, if the non-nucleic acid adjuvant on its own induces a Th2 response, the addition of CpG oligonucleotide can overcome this Th2 bias and induce a Th1 response that may be even more Th1-like than with CpG alone.

The combination of adjuvants may be administered simultaneously or sequentially. When the adjuvants are administered simultaneously they can be administered in the same or separate formulations, and in the latter case at the same or separate sites, but are administered at the same time. The adjuvants are administered sequentially, when the administration of the at least two adjuvants is temporally separated. The separation in time between the administration of the two adjuvants may be a matter of minutes or it may be longer. The separation in time is less than 14 days, and more preferably less than 7 days, and most preferably less than 1 day. The separation in time may also be with one adjuvant at prime and one at boost, or one at prime and the combination at boost, or the combination at prime and one at boost.

For use in the instant invention, the nucleic acids can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051–4054, 1986; Froehler et al., *Nucl. Acid. Res.* 14:5399–5407, 1986, ; Garegg et al., *Tet. Let.* 27:4055–4058, 1986, Gaffney et al., *Tet. Let.* 29:2619–2622, 1988). These chemistries can be performed by a variety of automated oligonucleotide synthesizers available in the market. Alternatively, CpG dinucleotides can be produced on a large scale in plasmids, (see Sambrook, T., et al., *Molecular Cloning: A Laboratory Manual*, Cold Spring Harbor laboratory Press, New York, 1989) which after being administered to a subject are degraded into oligonucleotides. Such plasmids may also encode other genes to be expressed such as an antigen-encoding gene in the case of a DNA vaccine. Oligonucleotides can be prepared from existing nucleic acid sequences (e.g., genomic or cDNA) using known techniques, such as those employing restriction enzymes, exonucleases or endonucleases.

For use in vivo, nucleic acids are preferably relatively resistant to degradation (e.g., via endo-and exo-nucleases). Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl-and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A., *Chem. Rev.* 90:544, 1990; Goodchild, J., *Bioconjugate Chem.* 1:165, 1990).

For administration in vivo, nucleic acids may be associated with a molecule that results in higher affinity binding to target cell (e.g., B-cell, monocytic cell and natural killer (NK) cell) surfaces and/or increased cellular uptake by target cells to form a "nucleic acid delivery complex." Nucleic acids can be ionically or covalently associated with appropriate molecules using techniques which are well known in the art. A variety of coupling or cross-linking agents can be used, e.g., protein A, carbodiimide, and N-succinimidyl-3-(2-pyridyldithio) propionate (SPDP). Nucleic acids can alternatively be encapsulated in liposomes or virosomes using well-known techniques.

Nucleic acids containing an appropriate unmethylated CpG can be effective in any mammal, preferably a human. Different nucleic acids containing an unmethylated CpG can cause optimal immune stimulation depending on the mammalian species. Thus an oligonucleotide causing optimal stimulation in humans may not cause optimal stimulation in a mouse and vice versa. One of skill in the art can identify the optimal oligonucleotides useful for a particular mammalian species of interest using routine assays described herein and/or known in the art.

The CpG ODN of the invention stimulate cytokine production (e.g., IL-6, IL-1 2, IFN-γ, TNF-α and GM-CSF) and B-cell proliferation in PBMC's taken from a subject such as a human. Specific, but nonlimiting examples of such sequences include those presented in Table 1 below:

TABLE 1

| sequences | |
|---|---|
| GCTAGACGTTAGCGT; | (SEQ ID NO: 1) |
| GCTAGATGTTAGCGT; | (SEQ ID NO: 2) |
| GCTAGACGTTAGCGT; | (SEQ ID NO: 3) |
| GCTAGACGTTAGCGT; | (SEQ ID NO: 4) |
| GCATGACGTTGAGCT; | (SEQ ID NO: 5) |
| ATGGAAGGTCCAGCGTTCTC; | (SEQ ID NO: 6) |
| ATCGACTCTCGAGCGTTCTC; | (SEQ ID NO: 7) |
| ATCGACTCTCGAGCGTTCTC; | (SEQ ID NO: 8) |
| ATCGACTCTCGAGCGTTCTC; | (SEQ ID NO: 9) |
| ATGGAAGGTCCAACGTTCTC; | (SEQ ID NO: 10) |
| GAGAACGCTGGACCTTCCAT; | (SEQ ID NO: 11) |
| GAGAACGCTCGACCTTCCAT; | (SEQ ID NO: 12) |
| GAGAACGCTCGACCTTCGAT; | (SEQ ID NO: 13) |
| GAGAACGCTGGACCTTCCAT; | (SEQ ID NO: 14) |
| GAGAACGATGGACCTTCCAT; | (SEQ ID NO: 15) |
| GAGAACGCTCCAGCACTGAT; | (SEQ ID NO: 16) |
| TCCATGTCGGTCCTGATGCT; | (SEQ ID NO: 17) |
| TCCATGTCGGTCCTGATGCT; | (SEQ ID NO: 18) |
| TCCATGACGTTCCTGATGCT; | (SEQ ID NO: 19) |
| TCCATGTCGGTCCTGCTGAT; | (SEQ ID NO: 20) |
| TCAACGTT; | (SEQ ID NO: 21) |
| TCAGCGCT; | (SEQ ID NO: 22) |
| TCATCGAT; | (SEQ ID NO: 23) |
| TCTTCGAA; | (SEQ ID NO: 24) |
| CAACGTT; | (SEQ ID NO: 25) |
| CCAACGTT; | (SEQ ID NO: 26) |
| AACGTTCT; | (SEQ ID NO: 27) |
| TCAACGTC; | (SEQ ID NO: 28) |
| ATGGACTCTCCAGCGTTCTC; | (SEQ ID NO: 29) |
| ATGGAAGGTCCAACGTTCTC; | (SEQ ID NO: 30) |
| ATCGACTCTCGAGCGTTCTC; | (SEQ ID NO: 31) |
| ATGGAGGCTCCATCGTTCTC; | (SEQ ID NO: 32) |
| ATCGACTCTCGAGCGTTCTC; | (SEQ ID NO: 33) |
| ATCGACTCTCGAGCGTTCTC; | (SEQ ID NO: 34) |
| TCCATGTCGGTCCTGATGCT; | (SEQ ID NO: 35) |
| TCCATGCCGGTCCTGATGCT; | (SEQ ID NO: 36) |
| TCCATGGCGGTCCTGATGCT; | (SEQ ID NO: 37) |
| TCCATGACGGTCCTGATGCT; | (SEQ ID NO: 38) |
| TCCATGTCGATCCTGATGCT; | (SEQ ID NO: 39) |
| TCCATGTCGCTCCTGATGCT; | (SEQ ID NO: 40) |
| TCCATGTCGTCCCTGATGCT; | (SEQ ID NO: 41) |
| TCCATGACGTGCCTGATGCT; | (SEQ ID NO: 42) |
| TCCATAACGTTCCTGATGCT; | (SEQ ID NO: 43) |
| TCCATGACGTCCCTGATGCT; | (SEQ ID NO: 44) |
| TCCATCACGTGCCTGATGCT; | (SEQ ID NO: 45) |
| GGGGTCAACGTTGACGGGG; | (SEQ ID NO: 46) |
| GGGGTCAGTCGTGACGGGG; | (SEQ ID NO: 47) |
| GCTAGACGTTAGTGT; | (SEQ ID NO: 48) |
| TCCATGTCGTTCCTGATGCT; | (SEQ ID NO: 49) |
| ACCATGGACGATCTGTTTCCCCTC; | (SEQ ID NO: 50) |
| TCTCCCAGCGTGCGCCAT; | (SEQ ID NO: 51) |
| ACCATGGACGAACTGTTTCCCCTC; | (SEQ ID NO: 52) |
| ACCATGGACGAGCTGTTTCCCCTC; | (SEQ ID NO: 53) |
| ACCATGGACGACCTGTTTCCCCTC; | (SEQ ID NO: 54) |
| ACCATGGACGTACTGTTTCCCCTC; | (SEQ ID NO: 55) |
| ACCATGGACGGTCTGTTTCCCCTC; | (SEQ ID NO: 56) |
| ACCATGGACGTTCTGTTTCCCCTC; | (SEQ ID NO: 57) |
| CACGTTGAGGGGCAT; | (SEQ ID NO: 58) |
| TCAGCGTGCGCC; | (SEQ ID NO: 59) |
| ATGACGTTCCTGACGTT; | (SEQ ID NO: 60) |
| TCTCCCAGCGGGCGCAT; | (SEQ ID NO: 61) |
| TCCATGTCGTTCCTGTCGTT; | (SEQ ID NO: 62) |
| TCCATAGCGTTCCTAGCGTT; | (SEQ ID NO: 63) |
| TCGTCGCTGTCTCCCCTTCTT; | (SEQ ID NO: 64) |
| TCCTGACGTTCCTGACGTT; | (SEQ ID NO: 65) |
| TCCTGTCGTTCCTGTCGTT; | (SEQ ID NO: 66) |
| TCCATGTCGTTTTGTCGTT; | (SEQ ID NO: 67) |
| TCCTGTCGTTCCTTGTCGTT; | (SEQ ID NO: 68) |
| TCCTTGTCGTTCCTGTCGTT; | (SEQ ID NO: 69) |
| TCCTGTCGTTTTTTGTCGTT; | (SEQ ID NO: 70) |
| TCGTCGCTGTCTGCCCTTCTT; | (SEQ ID NO: 71) |
| TCGTCGCTGTTGTCGTTTCTT; | (SEQ ID NO: 72) |
| TCCATGCGTGCGTGCGTTTT; | (SEQ ID NO: 73) |
| TCCATGCGTTGCGTTGCGTT; | (SEQ ID NO: 74) |
| TCCACGACGTTTTCGACGTT; | (SEQ ID NO: 75) |
| TCGTCGTTGTCGTTGTCGTT; | (SEQ ID NO: 76) |
| TCGTCGTTTTGTCGTTTTGTCGTT; | (SEQ ID NO: 77) |
| TCGTCGTTGTCGTTTTGTCGTT; | (SEQ ID NO: 78) |
| GCGTGCGTTGTCGTTGTCGTT; | (SEQ ID NO: 79) |
| TGTCGTTTGTCGTTTGTCGTT; | (SEQ ID NO: 80) |
| TGTCGTTGTCGTTGTCGTTGTCGTT; | (SEQ ID NO: 81) |
| TGTCGTTGTCGTTGTCGTT; | (SEQ ID NO: 82) |
| TCGTCGTCGTCGTT; | (SEQ ID NO: 83) |
| TGTCGTTGTCGTT; | (SEQ ID NO: 84) |
| TCCATAGCGTTCCTAGCGTT; | (SEQ ID NO: 85) |
| TCCATGACGTTCCTGACGTT; | (SEQ ID NO: 86) |
| GTCGYT; | (SEQ ID NO: 87) |

TABLE 1-continued sequences

| | |
|---|---|
| TGTCGYT; | (SEQ ID NO: 88) |
| AGCTATGACGTTCCAAGG; | (SEQ ID NO: 89) |
| TCCATGACGTTCCTGACGTT; | (SEQ ID NO: 90) |
| ATCGACTCTCGAACGTTCTC; | (SEQ ID NO: 91) |
| TCCATGTCGGTCCTGACGCA; | (SEQ ID NO: 92) |
| TCTTCGAT; | (SEQ ID NO: 93) |
| ATAGGAGGTCCAACGTTCTC; | (SEQ ID NO: 94) |
| GTCGTT | (SEQ ID NO: 95) |
| GTCGTC | (SEQ ID NO: 96) |
| TGTCGTT | (SEQ ID NO: 97) |
| TGTCGCT | (SEQ ID NO: 98) |

Preferred CpG ODN can effect at least about 500 pg/ml of TNF-α, 15 pg/ml IFN-γ, 70 pg/ml of GM-CSF 275 pg/ml of IL-6, 200 pg/ml IL-12, depending on the therapeutic indication. These cytokines can be measured by assays well known in the art. The oligonucleotides listed above or other preferred CpG ODN can effect at least about 10%, more preferably at least about 15% and most preferably at least about 20% YAC-1 cell specific lysis or at least about 30%, more preferably at least about 35%, and most preferably at least about 40% 2C11 cell specific lysis, in assays well known in the art.

The term "effective amount" of a CpG oligonucleotide refers to the amount necessary or sufficient to realize a desired biologic effect. For example, an effective amount of an oligonucleotide containing at least one unmethylated CpG and a non-nucleic acid adjuvant for treating an infectious disorder is that amount necessary to cause the development of an antigen specific immune response upon exposure to the microbe, thus causing a reduction in the amount of microbe within the subject and preferably to the eradication of the microbe. The effective amount for any particular application can vary depending on such factors as the disease or condition being treated, the particular CpG oligonucleotide being administered (e.g. the number of unmethylated CpG motifs or their location in the nucleic acid), the size of the subject, or the severity of the disease or condition. One of ordinary skill in the art can empirically determine the effective amount of a particular adjuvant and antigen without necessitating undue experimentation.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the adjuvant combination can be administered to a subject by any mode allowing the oligonucleotide to be taken up by the appropriate target cells. "Administering" the pharmaceutical composition of the present invention may be accomplished by any means known to the skilled artisan. Preferred routes of administration include but are not limited to oral, transdermal (e.g. via a patch), parenteral injection (subcutaneous, intradermal, intravenous, parenteral, intraperitoneal, intrathecal, etc.), or mucosal intranasal, intratracheal, inhalation, and intrarectal, intravaginal etc). An injection may be in a bolus or a continuous infusion.

For example the pharmaceutical compositions according to the invention are often administered by intramuscular or intradermal injection, or other parenteral means, or by biolistic "gene-gun" application to the epidermis. They may also be administered by intranasal application, inhalation, topically, intravenously, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science* 249:1527–1533, 1990, which is incorporated herein by reference.

The pharmaceutical compositions are preferably prepared and administered in dose units. Liquid dose units are vials or ampoules for injection or other parenteral administration. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administration of doses at specific intervals of weeks or months apart is usual for boosting the antigen-specific responses.

The adjuvants and antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid-group.

Suitable buffering agents include: acetic acid and a salt (1–2% w/v); citric acid and a salt (1–3% w/v); boric acid and a salt (0.5–2.5% w/v); and phosphoric acid and a salt (0.8–2% w/v). Suitable preservatives include benzalkonium chloride (0.003–0.03% w/v); chlorobutanol (0.3–0.9% w/v); parabens (0.01–0.25% w/v) and thimerosal (0.004–0.02% w/v).

The pharmaceutical compositions of the invention contain an effective amount of a combination of adjuvants and antigens optionally included in a pharmaceutically-acceptable carrier. The term "pharmaceutically-acceptable carrier" means one or more compatible solid or liquid filler, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

Compositions suitable for parenteral administration conveniently comprise sterile aqueous preparations, which can be isotonic with the blood of the recipient. Among the acceptable vehicles and solvents are water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The adjuvants or antigens useful in the invention may be delivered in mixtures of more than two adjuvants or antigens. A mixture may consist of several adjuvants in addition to the synergistic combination of adjuvants or several antigens.

A variety of administration routes are available. The particular mode selected will depend, of course, upon the particular adjuvants or antigen selected, the age and general health status of the subject, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and triglycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within amatrix such as those described in U.S. Pat. Nos. 4,452,775, 4,675,189, and 5,736, 152, and (b) diffusional systems in which an active component permeates at a controlled rate from a polymer such as described in U.S. Pat. Nos. 3,854,480, 5,133,974 and 5,407, 686. In addition, pump-based hardware delivery systems can be used, some of which are adapted for implantation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

The use of CpG ODN as an adjuvant alone or in combination with other adjuvants was evaluated. The hepatitis B virus surface antigen (HBsAg) given as a recombinant protein or expressed in vivo from a DNA vaccine was used as an exemplary model system in the Examples set forth below.

MATERIALS AND METHODS

Animals

Experiments on adult mice were carried out using female BALB/c mice (Charles River, Montreal, QC) at 6–8 weeks of age.

Newborn mice were obtained through breeding male and female BALB/c mice (Charles River) in the Loeb animal facility (Loeb Health Research Institute, The Ottawa Hospital, Ottawa, ON). Pregnant females were monitored daily to ensure accurate recording of the date of birth. Both male and female neonates were used for immunization.

Cynomolgus monkeys (1.5–3 kg) were housed at the Primate Research Center, Bogor, Indonesia.

Orantutans (5–20kg) were housed at Wanariset Station for the Orangutan Reintroduction Program of the Indonesian government, Balikpapan, Kalimantan.

HBsAg Subunit Vaccination of Mice

The subunit vaccine consisted of HBsAg (ay subtype) which had been produced as a recombinant protein in yeast cells (Medix Biotech #ABH0905). This was diluted in saline for use without adjuvant. HBsAg was also formulated with alum and/or CpG ODN as adjuvant. HBsAg protein was mixed with aluminum hydroxide (Alhydrogel 85, [$Al_2O_3$], Superfos Biosector, Vedbaek, Denmark) in the same ratio of 25 mg $A^{3+}$ per mg protein as used in the commercial vaccines (i.e., 2.5 12% $Al_2O_3$ per μg HBsAg). The protein and alum were mixed with a vortex and then left on ice for at least 30 minutes prior to use to allow the protein to adsorb onto the $Al_2O_3$. This solution was mixed again immediately prior to injection by drawing up into the syringe 3–5 times.

For groups treated with CpG ODN, an appropriate volume of synthetic oligodeoxynucleotide (ODN # 1826) of the sequence TCCATGACGTTCCTGACGTT (SEQ ID NO. 86) synthesized with a phosphorothioate backbone (Oligos Etc. & Oligo Therapeutics, Wilsonville, Oreg.) was added alone or with alum to HBsAg on the day of injection. Adult mice received a single intramuscular (IM) injection into the left tibialis anterior (TA) muscle of 1 or 2 ug HBsAg, without or with adjuvant (alum and/or CpG ODN), in 50 1 vehicle. When CpG DNA was added, each animal received a total of 1, 10, 100 or 500 μg ODN. Newborn mice were immunized within 24 hours of birth or 7 days after birth by bilateral injection of a total of 1 μg HBsAg into the posterior thigh muscles (2×101 α@ 0.05 mg/ml). All injections were carried out with a 0.3 ml insulin syringe which has a fused 29G needle (Becton Dickenson, Franklin Lakes, N.J.). For injection of adults, the needle was fitted with a collar of polyethylene (PE) tubing to limit penetration of the needle to about 3 mm. All intramuscular injections were carried out through the skin (shaved for adults) and under general anesthesia (Halothane, Halocarbon Laboratories, River Edge, N.J.).

HBsAg Subunit Vaccination of Monkeys

Monkeys were immunized by IM injection into the anterior thigh muscle of Engerix-B® (SmithKline Beecham Biologicals, Rixensart, BE) which comprises HBsAg (ay subtype, 20 µg/ml) adsorbed to alum (25 mg Al3+/mg HbsAg). Each monkey received an injection of 0.5 ml containing 10 µg HbsAg. For some monkeys, 500 µg CpG ODN 1968 (TCGTCGCTGTTGTCGTTTCTT) (SEQ ID NO 72) was added to the vaccine formulation.

HBsAg Subunit Vaccination of Orangutans

Orangutans were immunized by IM injection into the anterior thigh muscle of HBsAg *ay subtype, 20 µg/ml) combined with alum (25 mg Al3+/mg HBsAg), combined with CpG. CpG ODN 2006 (TCGTCGTGTCGTGTCGTT) (SEQ ID NO 77) was added to the vaccine formulation. Each orangutan received an injection of 1.0 ml containing 20 µg HBsAg with alum (500 µg), CpG oligonucleotide (1 mg) or both adjuvants.

Experimental Groups
Comparison of CpG ODN and Non-nucleic Acid Adjuvants with HBsAg Subunit Vaccine Twelve groups of adult BALB/c mice (n=10) were injected with 1 µg HBsAg (i) alone, (ii) mixed with alum, (iii, iv, v, vi, vii) mixed with 0.1, 1, 10, 100 or 500 µg CpG ODN, or (viii, ix, x, xi, xii) mixed with both alum and 0.1, 1, 10, 100 or 500 µg CpG ODN. These mice were bled at 1, 2, 4 and 8 weeks after immunization and the plasma was assayed for anti-HBs. At the end of the study the mice were killed and their spleens removed for assay of CTL activity.

Other groups of mice (n=5) were immunized with HBsAg (1 µg) alone, with alum (25 µg A13+), with one of several different CpG and non-CpG control oligonucleotides of different backbones (10 µg), or with both alum and an oligonucleotide.

Other groups of mice (n=5) were immunized as above (except only the 10 µg dose of CpG ODN was used) and boosted with the identical or a different formulation at 8 weeks, then spleens were removed 2 weeks later for evaluation of CTL activity.

Other groups of mice were immunized with HBsAg (1 µg) and one of the following non-nucleic acid adjuvants alone or in combination with CpG ODN (10 µg): monophosphoryl lipid A (MPL, 50 µg, Ribi); Freund's Complete Adjuvant (CFA; 1:1 v/v); Freund's Incomplete Adjuvant (IFA; 1:1 v/v).

Immunization of Neonates with Subunit or DNA Vaccine

Groups of newborn and young BALB/c mice (n=10) aged <24 hours, 3, 7 or 14 days were injected with (i, ii, iii) a total of 1 µg HBsAg with alum, with CpG ODN 1826 (10 µg) or with both alum and CpG ODN, or with (iv) an HBsAg-expressing DNA vaccine (1-µg pCMV-S). Plasma was obtained at 4, 8, 12 and 16 weeks for assay of anti-HBs as total IgG and IgG subtypes (IgG1 and IgG2a). At the end of the study the mice were killed and their spleens removed for assay of CTL activity.

Immunization of Cynomolgus Monkeys with HBsAg and Alum or Alum+CpG ODN

Two groups of juvenile Cynomolgus monkeys (n=5) were immunized at 0 and 10 weeks with 0.5 ml Engerix-B (HBsAg at 20 mg/ml adsorbed to alum, 25 mg Al3+/mg HBsAg) to which had been added saline (0.1 ml) or CpG ODN 2006 (500 µg in 0.1 ml, SEQ #77). Monkeys were bled at 2, 8, 10, 12 and 14 weeks and plasma was evaluated for anti-HBs titers (mIU/ml).

Immunization of Orangutans with HBsAg and Alum or CpG ODN or Alum+CpG ODN

Three groups of juvenile orangutans were immunized IM at 0 and 4 weeks with 1 ml of vaccine containing HBsAg (10 µg) plus (i) alum (25 mg Al3+/mg HBsAg)(n=13), (ii) CpG ODN 2006 (SEQ# 77) (m=24) or (iii) alum plus CpG ODN (n=14). Animals were bled at 4,8 and 12 weeks and plasma was evaluated for anti-HBs titers (mIU/ml).

Evaluation of Humoral Response to HBsAg

Mice: Heparinized blood was collected by retrobulbar puncture of lightly anaesthetized mice as described elsewhere (Michel et al., 1995). Plasma was recovered by centrifugation (7 min @ 13,000 rpm). Antibodies specific to HBsAg in plasma were detected and quantified by end-point dilution ELISA assay (in triplicate) on individual samples. Ten-fold serial dilutions of plasma were first added to 96-well microtiter plates with a solid phase consisting of plasma-derived HBsAg particles (100 L/well of HBsAg ay subtype at 1 g/ml, coated overnight at RT) and incubated for 1 hr at 37C. The bound antibodies were then detected by incubation for 1 hr at 37C with HRP-conjugated goat anti-mouse IgG, IgM, IgG1 or IgG2a (1:4000 in PBS-Tween, 10% FCS; 100 l/well, Southern Biotechnology Inc., Birmingham, Ala.), followed by incubation with OPD solution (100 l/well, Sigma, St. Louis, Mo.) for 30 minutes at RT in the dark. The reaction was stopped by the addition of sulfuric acid (50 1 of 4N $H_2SO_4$). End-point titers were defined as the highest plasma dilution that resulted in an absorbance value (OD 450) two times greater than that of non-immune plasma with a cut-off value of 0.05. Anti-HBs titers were expressed as group means of individual animal values, which were themselves the average of triplicate assays.

Primates: Monkeys and orangutans were bled by antecubital venous puncture into heparinized tubes and plasma was recovered by centrifugation (7 min @ 13,000 rpm). Plasma was then evaluated for anti-HBs titers using a commercial kit (Monolisa anti-HBs, Pasteur-Sanofi) and expressed in milli-International Units per milliliter (mIU/ml) by comparison with standards defined by the World Health Organization. A titer of 10 mIU/ml is considered sufficient to confer protection to humans and great apes against infection by HBV.

Evaluation of Cytotoxic T cell Response to HBsAg in Mice

Cytotoxic T-lymphocyte (CTL) activity was determined using splenocytes taken from mice 4 or 8 weeks post-prime or post-boost. In brief, single cell suspensions were prepared and suspended in tissue culture medium (RPMI 1640, 10% FBS, Life Technologies, Grand Island, N.Y., supplemented with $5 \times 10^{-5}$ M β-mercaptoethanol and penicillinstreptomycin solution, 1000 U/ml, 1 mg/ml fmal concentrations respectively, Sigma, and 3% El-4 supernatant as a source of IL-2). Splenocytes ($3 \times 10^7$) were co-cultured for 5 days (37° C., 5% CO2) with $1 \times 10^6$ syngenic HBsAg-expressing stimulator cells (P815S) or control target cells (P815) in round bottom 96-well culture plates (37° C., 5% CO2, 4 hr). Supernatant (100 µl) was removed for radiation (gamma) counting. Spontaneous release was determined by incubating target cells without effector cells and total release by addition of 100 µl 2 N HCl to the target cells. The percent lysis was calculated as [(experimental release—spontaneous release)/(total release—spontaneous release)]×100. The percent specific lysis was calculated as % lysis with P815S-% lysis with P815 cells, CTL activity for responding mice [% specific lysis >10] were expressed as means±SEM of individual animal values, which were themselves the average of triplicate assays.

Example 1

Synergy of CpG ODN with Alum as Adjuvant for HBV Subunit Vaccine in Mice

A. Strength and Kinetics of Humoral Response

Immunization of BALB/c mice with HBsAg alone elicited only low titers of anti-HBs (<100) by 4 weeks. These titers were about 10-fold higher with the addition of alum as adjuvant, 60-fold higher with CpG ODN and more than 500-fold higher with both alum and CpG ODN. At later time points, the highest peak titers were with HBsAg/alum/CpG, the second highest with HBsAg/CpG, then HBsAg/alum (FIG. 1).

Figure 8:
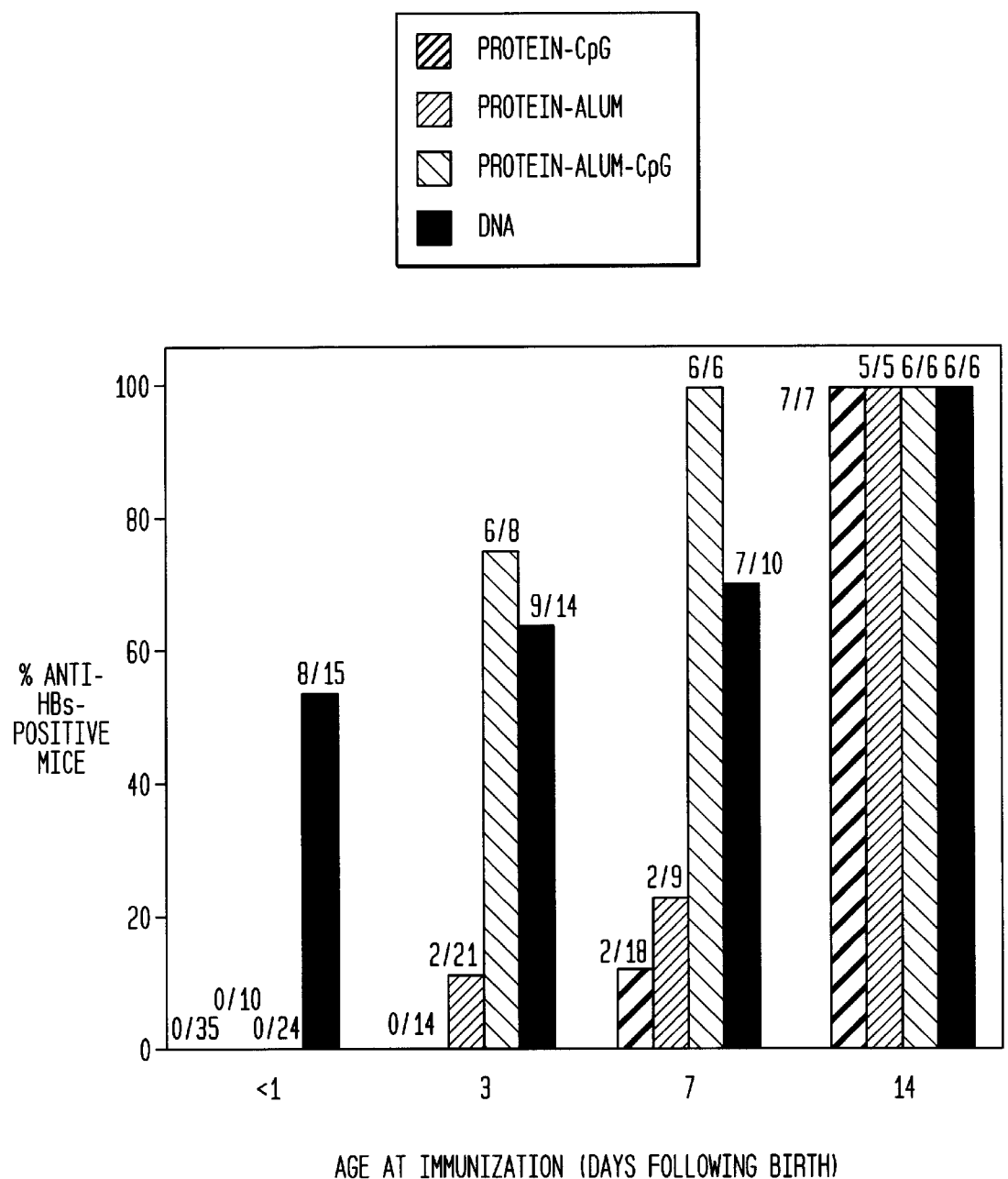
FIG. 8 is a graph of the percent of young BALB/c mice that seroconverted (end-point dilution titer >7100) after immunization at <1, 3, 7 or 14 days of age. Mice were immunized with 10 μg HBsAg-expressing DNA vaccine (pCMV-S), or with recombinant HBsAg (1 μg) with alum (25 mg Al3+/mg HBsAg), CpG ODN 1826 (10 μg) or both alum and CpG ODN. Each point represents the proportion of mice responding, the numbers above the bars show the number of responding over the total number immunized.
Figure 9:
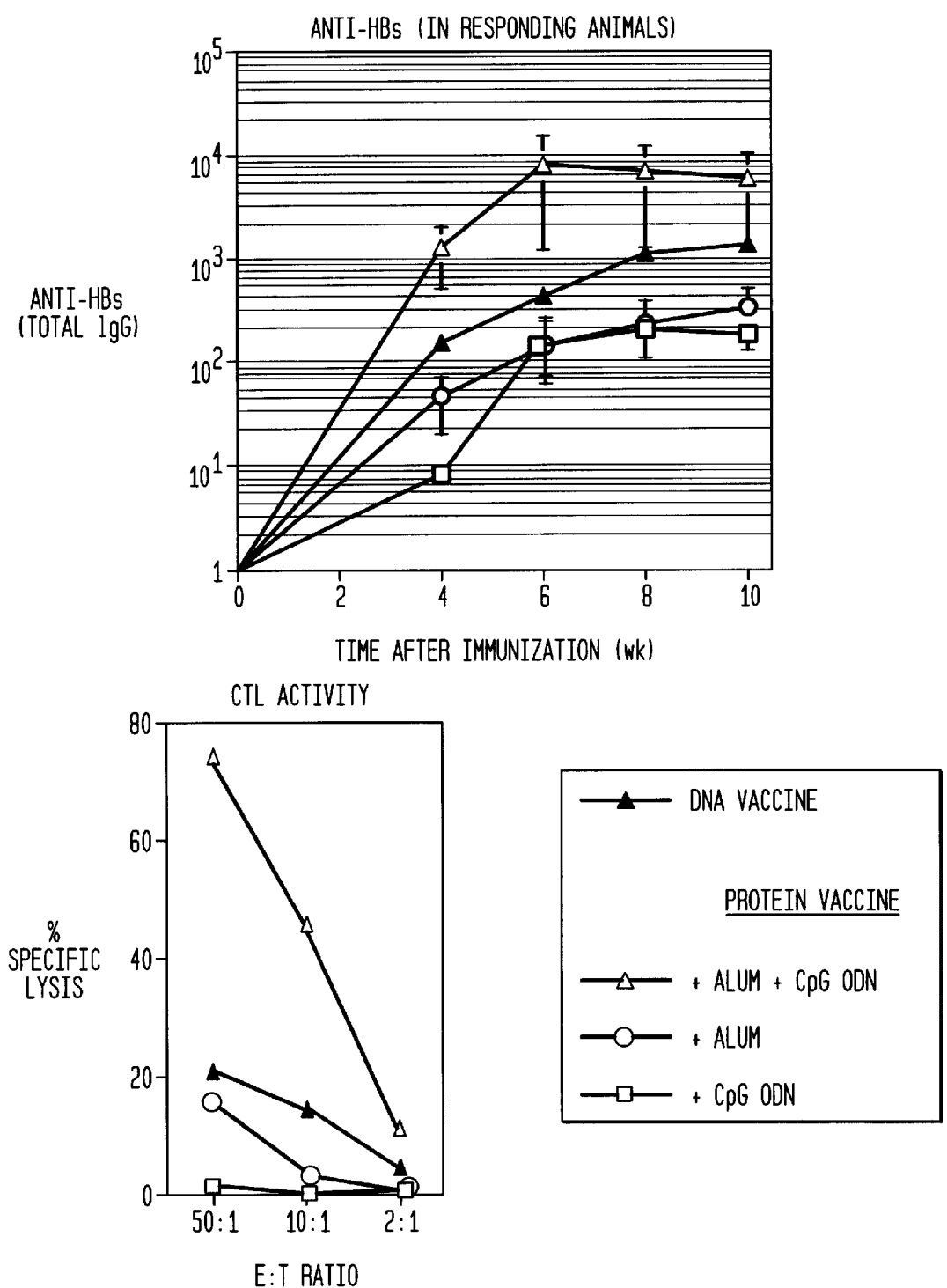
FIG. 9 has two graphs illustrating humoral and cytotoxic T-lymphocyte (CTL) responses in BALB/c mice immunized at 7 days of age with a DNA vaccine (1 μg pCMV-S), or with 1 μg recombinant HBsAg protein alone, adsorbed onto alum (25 mg Al$^{3+}$/mg HBsAg), with 100 μg of immunostimulatory CpG ODN 1826, or with both alum and CpG ODN. Upper panel: Each point represents the group mean of animals that seroconverted (see FIG. 8 for numbers of animals) for titers of anti-HBs (total IgG) as determined in triplicate by end-point dilution ELISA assay. End-point titers were defmed as the highest plasma dilution that resulted in an absorbance value (OD 450) two times greater than that of control non-immune plasma with a cut-off value of 0.05. Lower panel: Each point represents the mean % specific lysis at the indicated effector: target (E:T) cell ratio in a chromium release assay with HBsAg-expressing cells as targets.

Similar synergistic results for antibody responses were obtained when immunization against HBsAg was carried out in neonatal and very young mice, in which the immune system is immature. In mice immunized at 3 days of age, where the immune system is even less mature than a newborn human, 10% and 0% of mice seroconverted with alum and CpG ODN alone respectively, but 75% seroconverted when CpG ODN and alum were used together. In 7 day old mice, which have an immune system similar in maturity to that of a newborn human, seroconversion for alum, CpG or the combination was 11%, 22% and 1 00% respectively (FIG. 8). Furthermore, in these 7 day old mice, antibody titers were up to 80-fold higher with the combined adjuvants than with either adjuvant alone (FIG. 9).

Figure 2:
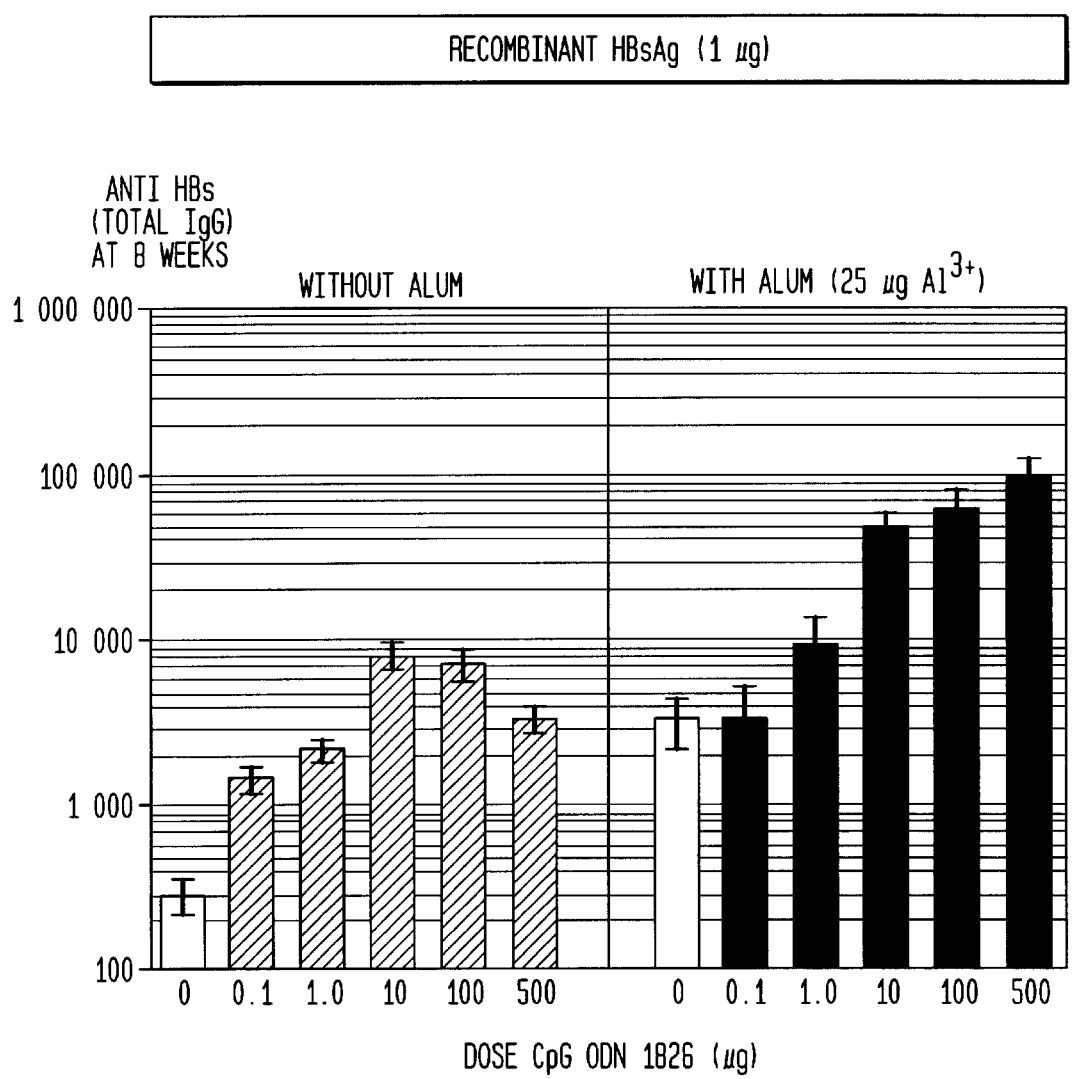
FIG. 2 is a graph illustrating humoral responses in adult BALB/c mice immunized with 1 μg recombinant HBsAg protein, with or without alum, and with 0, 0.1, 1, 10, 100 or 500 μg of CpG ODN 1826 added. Each point represents the group mean (n=10) for anti-HBs titers (total IgG) as determined by end-point dilution ELISA assay.

When used alone or combined with alum, there is a dose-response for CpG ODN with the best results being obtained with an intermediate dose (10 μg) and no further or only relatively small gains with higher doses (up to 500 μg) when used alone or combined with alum respectively (FIG. 2).

Figure 3:
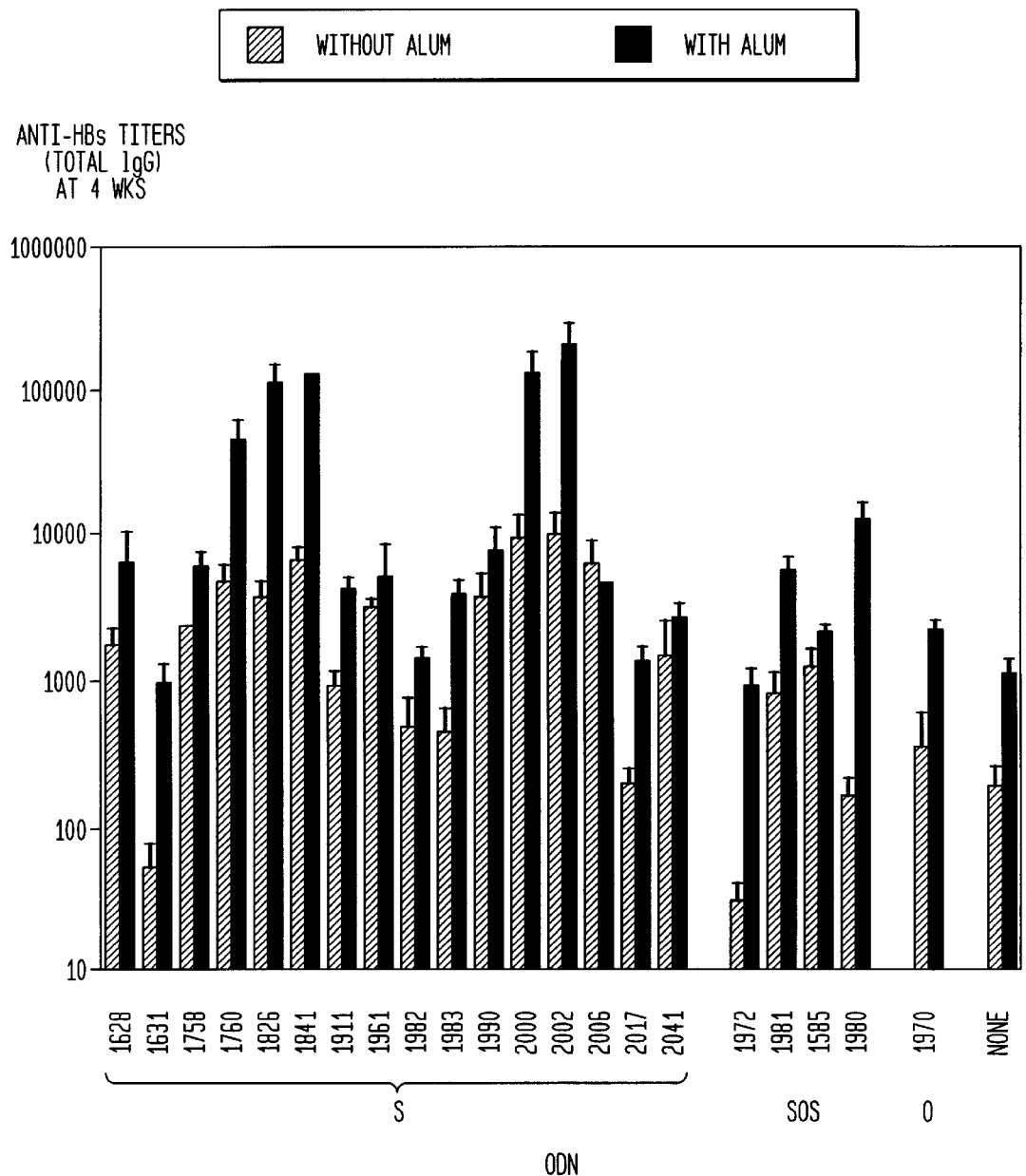
FIG. 3 is a graph illustrating humoral responses in adult BALB/c mice immunized with 1 μg recombinant HBsAg protein, with or without alum, and with one of several different oligonucleotides (ODN, 10 μg). The ODN were made with a natural phosphodiester backbone (O), synthetic phosphorothioate backbone (S) or a chimeric of phosphodiester center regions and phosphorothioate ends (SOS). Most of the ODN contained 1–3 CpG motifs but some of the ODN were non-CpG controls (1911, 1982, 2041). Each point represents the group mean (n=5) for anti-HBs titers (total IgG) as determined by end-point dilution ELISA assay.

When a large panel of ODN is compared for adjuvant activity it can be seen that CPG ODN with a nuclease-resistant phosphorothioate backbone have the best adjuvant effects (FIG. 3). There was very little or no adjuvant activity of non-CpG control ODN with a phosphorothioate backbone, or of CpG ODN with a chimeric or phosphodiester backbone. However, for those phosphorothioate CpG ODN that did not have adjuvant effect, all exhibited a synergistic effect with alum. In general, antibody titers with combined alum and CpG ODN were 10 to 100-fold higher than with CpG ODN and/or 100 to 1000-fold higher than with alum alone (FIG. 3).

B. Strength of Cytotoxic T-lymphocyte Response

CTL were very weak with HBsAg and no adjuvant, and were completely lost with the addition of alum. CTL were augmented equally with both CpG ODN as with combined alum and CpG ODN (FIG. 1). A synergy for CTL responses could be seen with prime-boost strategies, in that priming with CpG ODN and boosting with alum gave better CTL than priming and boosting with CpG alone (FIG. 4) (Note: use of alum alone completely abrogates the CTL response).

A synergistic action of CpG ODN and alum on CTL was very evident with immunization of young (7 day old) mice. In this case, neither alum nor CpG ODN used alone induced significant levels of HBsAg-specific CTL, but when used together there wre very strong CTL were observed (FIG. 9).

Thus, CpG ODN is superior to alum for both humoral and cell-mediated responses, when each is used alone as adjuvant with the HBsAg subunit vaccine in mice. When used together, there is a synergy of action such that antibody and CTL activity are stronger than when either adjuvant is used alone. These results indicate that CpG ODN could be used to replace alum in vaccine formulations, which could be desirable to avoid associated side-effects due to local irritation in the muscle, or for certain live-attenuated or multivalent vaccines where it is not possible to use alum because chemical interactions interfere with the efficacy of the vaccine. This should not occur with CpG ODN. Of even greater interest is the strong synergistic response when CpG ODN and alum are used together as adjuvants. This could allow better immune responses with lower or fewer doses of antigen. There is a fairly flat dose response to CpG ODN whether or not alum is present, indicating that a wide range of CpG ODN could be useful to adjuvant vaccines in humans.

Example 2

Synergy of CpG ODN with Other Non-nucleic Acid Adjuvants for HBV Subunit Vaccine in Mice.

As discussed above, CpG ODN alone gave 8-fold higher antibody titers than alum, the only adjuvant currently licensed for human use. It also produces superior results to monphosphoryl lipid A (MPL, Ribi Pharmaceuticals, Middleton, Wis.), a new adjuvant that is currently in human clinical trials even when administered in a dose of five times less than that of MPL. There was, as discussed above, a strong synergy with CpG ODN and alum, but in contrast no such synergy was seen with MPL and alum. Owing to the strong synergistic effect of alum and CpG ODN, this combination of adjuvants is even better than Freund's complete adjuvant (FCA) for inducing antibodies in mice (FIG. 5) Freund's, which is considered the gold standard adjuvant for animal models is much too toxic to use in humans.

Figure 6:
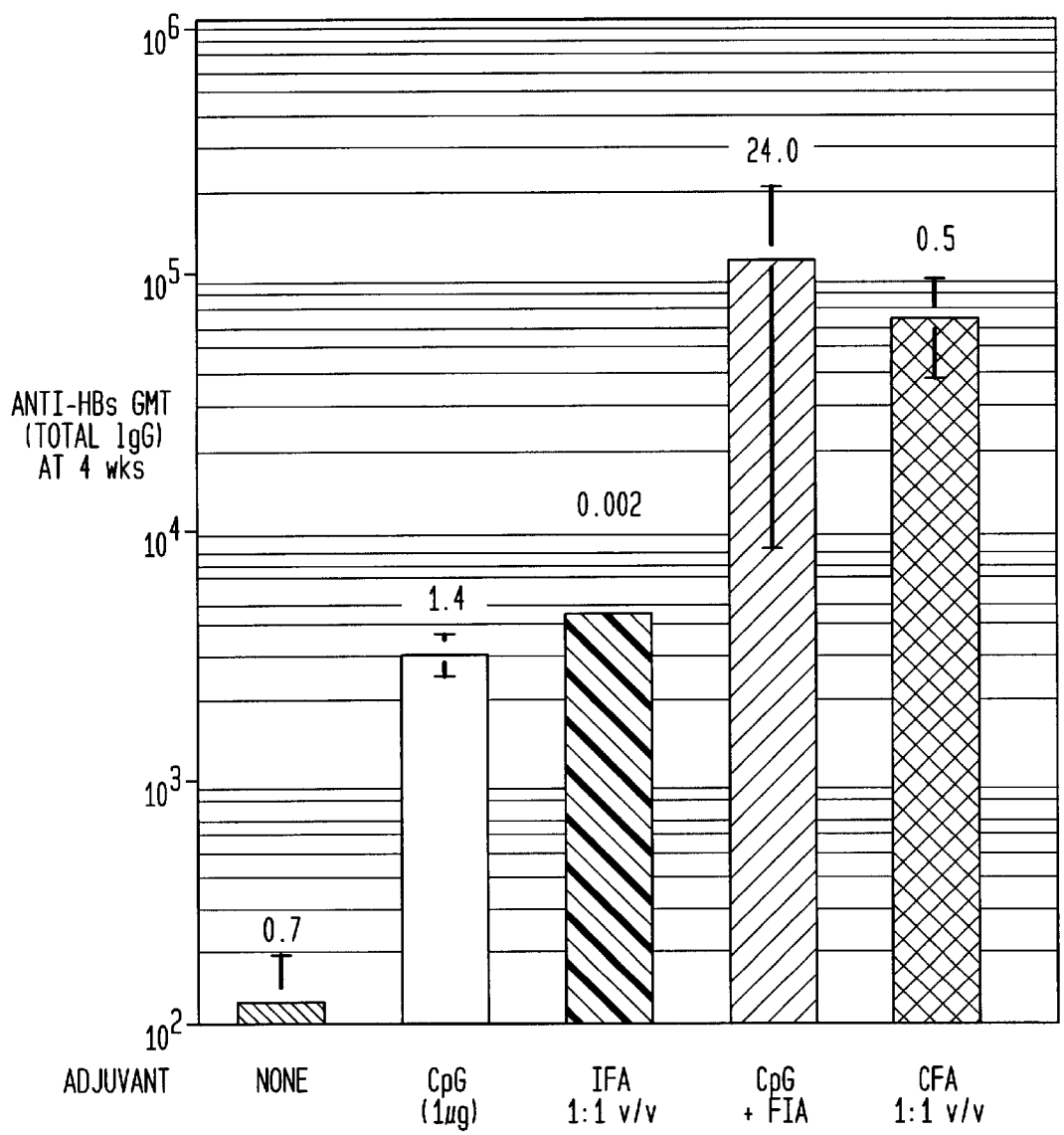
FIG. 6 is a bar graph depicting the amount of total IgG (end-point ELISA titer) produced at 4 weeks in BALB/c mice immunized with 1 μg of HBsAg with or without CpG and/or IFA (mineral oil mixed 1:1 v/v) or CFA (complete Freund's adjuvant mixed 1:1 v/v). The numbers above each bar indicate the IgG2a:IgG1 ratio, with a number in excess of 1 indicating a more Th1-like response.

The synergy seen with CpG ODN and alum, was also seen with CpG ODN combined with other adjuvants. When used alone, CpG ODN and Freund's incomplete adjuvant (FIA, a type of mineral oil) induced similar antibody titers, but when used together the anti-HBs titers were more than 50-fold higher than with either adjuvant alone. Indeed, the combination of CpG ODN and FIA was even better than FCA (FIG. 6).

Figure 7:
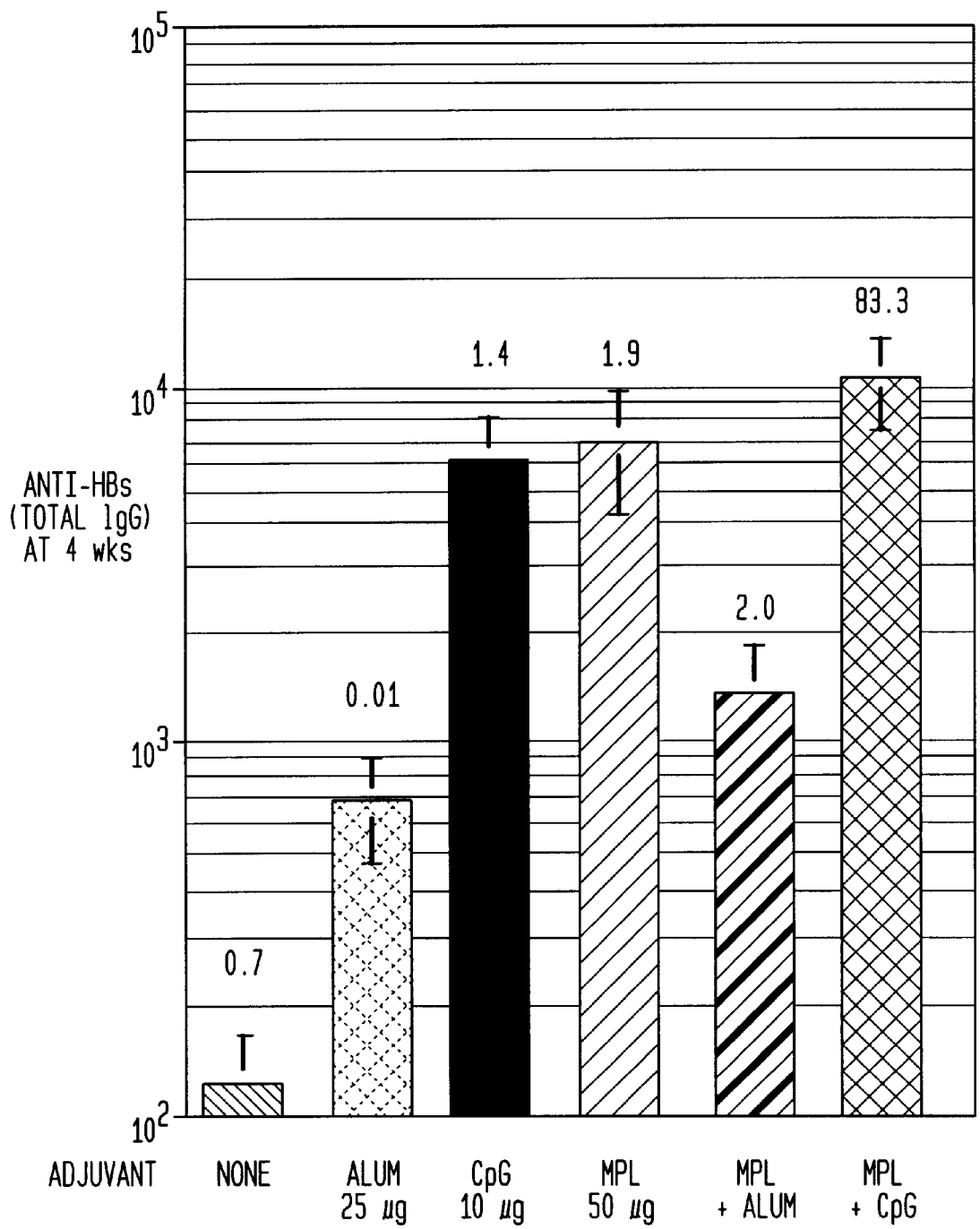
FIG. 7 is a bar graph depicting the amount of total IgG produced at 4 weeks in BALB/c mice immunized with 1 μg of HBsAg with or without CpG and/or MPL (monophosphoryl lipid A, 50 μg) or alum. The numbers above each bar indicate the IgG2a:IgG1 ratio, with a number in excess of 1 indicating a more Th1-like response.

Similarly, CpG ODN and MPL alone gave equally high antibody titers, but when used together the titers were about 4-times higher than with either adjuvant alone (FIG. 7). While the synergistic response with CpG and MPL was not as marked with respect to overall antibody titers, it was very pronounced with respect to the Th1-bias of these antibodies (see below).

Example 3

Figure 5:
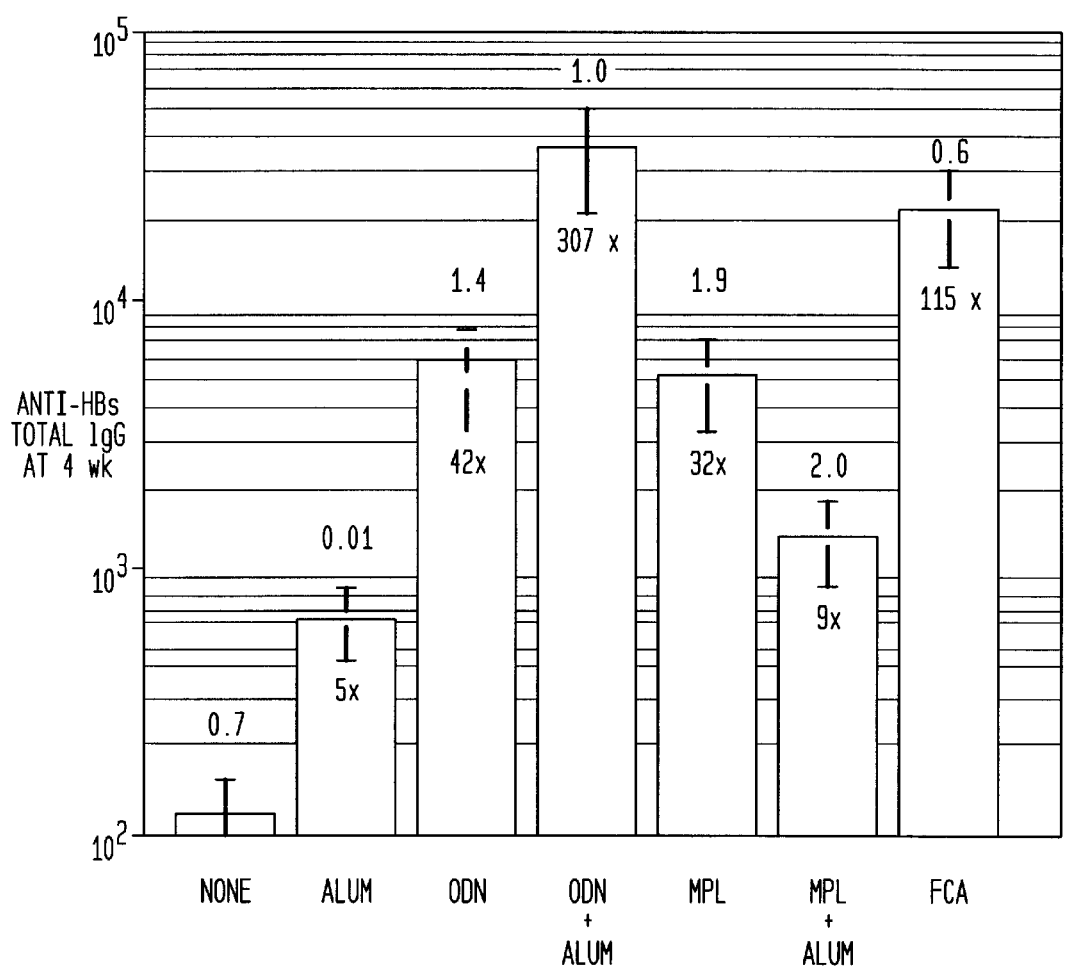
FIG. 5 is a graph of humoral responses in BALB/c mice immunized with HBsAg (1 μg) without adjuvant or with various adjuvants alone or in combination. The adjuvants were: alum (25 mg Al$^{3+}$/mg HBs/Ag), with CpG DNA (10 jig CpG ODN 1826), monophosphoryl lipid A (MPL, 50 μg) and Freund's complete adjuvant (mixed 1:1 v/v with HBsAg solution). Each point represents the group mean (n=0) for anti-HBS titers (total IgG) as determined by end-point dilution ELISA assay 4 weeks after immunization.

Dominance and Synergy of CpG ODN with Alum for Induction of a Th1-type immune response including CTL Immunization with either HBsAg alone or with alum induces a predominantly Th2-type humoral response with virtually no IgG2a antibodies, which are induced in response to Th1 -type cytokines such as IL-12 and IFN-γ. Rather, almost all (>99%) antibodies were of the IgG1 isotype IgG2a:IgG1=0.01. CpG ODN induces significantly more IgG2a antibodies, such that they made up at least 50% of the total IgG (IgG (IgG2a:IgG1=1.4). The combination of alum and CpG ODN induce an equally strong Th1 response as CpG ODN alone (IgG2a:IgG1=1.0), despite the extremely strong Th2-bias of alum (FIG. 5). Similarly CTL responses with CpG ODN plus alum were as strong as those with CpG ODN alone, despite the fact that the Th2-bias of alum resulted in a complete loss of CTL when alum was used alone (FIG. 1).

Figure 10:
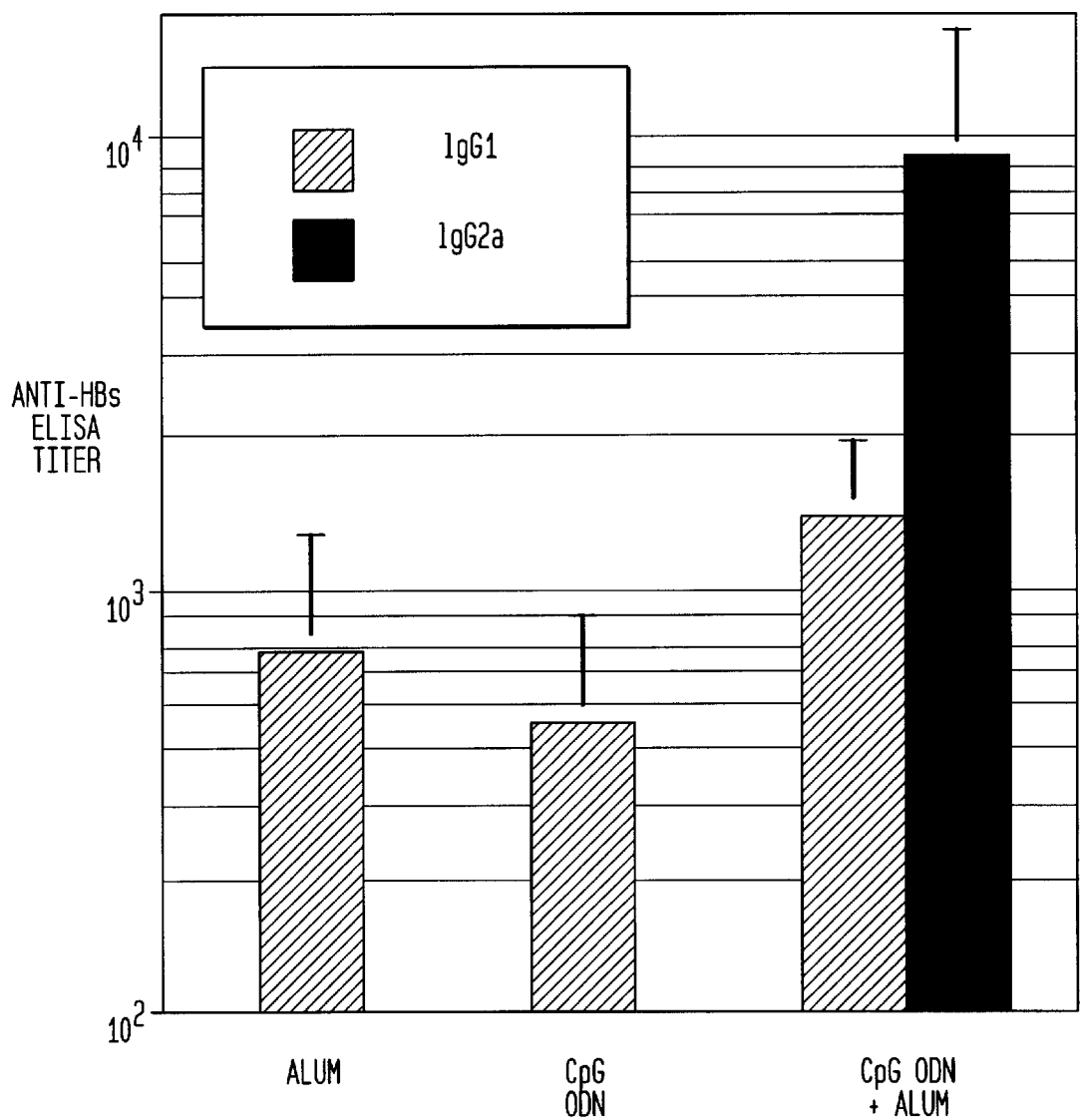
FIG. 10 is a bar graph illustrating humoral responses in neonatal BALB/c mice at 8 weeks after immunization (at 7 days of age) with 1 μg recombinant HBsAg protein with alum (25 mg Al$^{3+}$/mg HBsAg), with 10 μg of CpG ODN 1826, or with both alum and CpG ODN. Each point represents the group mean (see FIG. 8 for numbers of animals) for anti-HBs titers (IgG1 and IgG2a isotypes) as determined by end-point dilution ELISA assay. IgG1 antibodies indicate a Th2-biased response whereas IgG2a antibodies are indicative of a Th1-type response.
Figure 11:
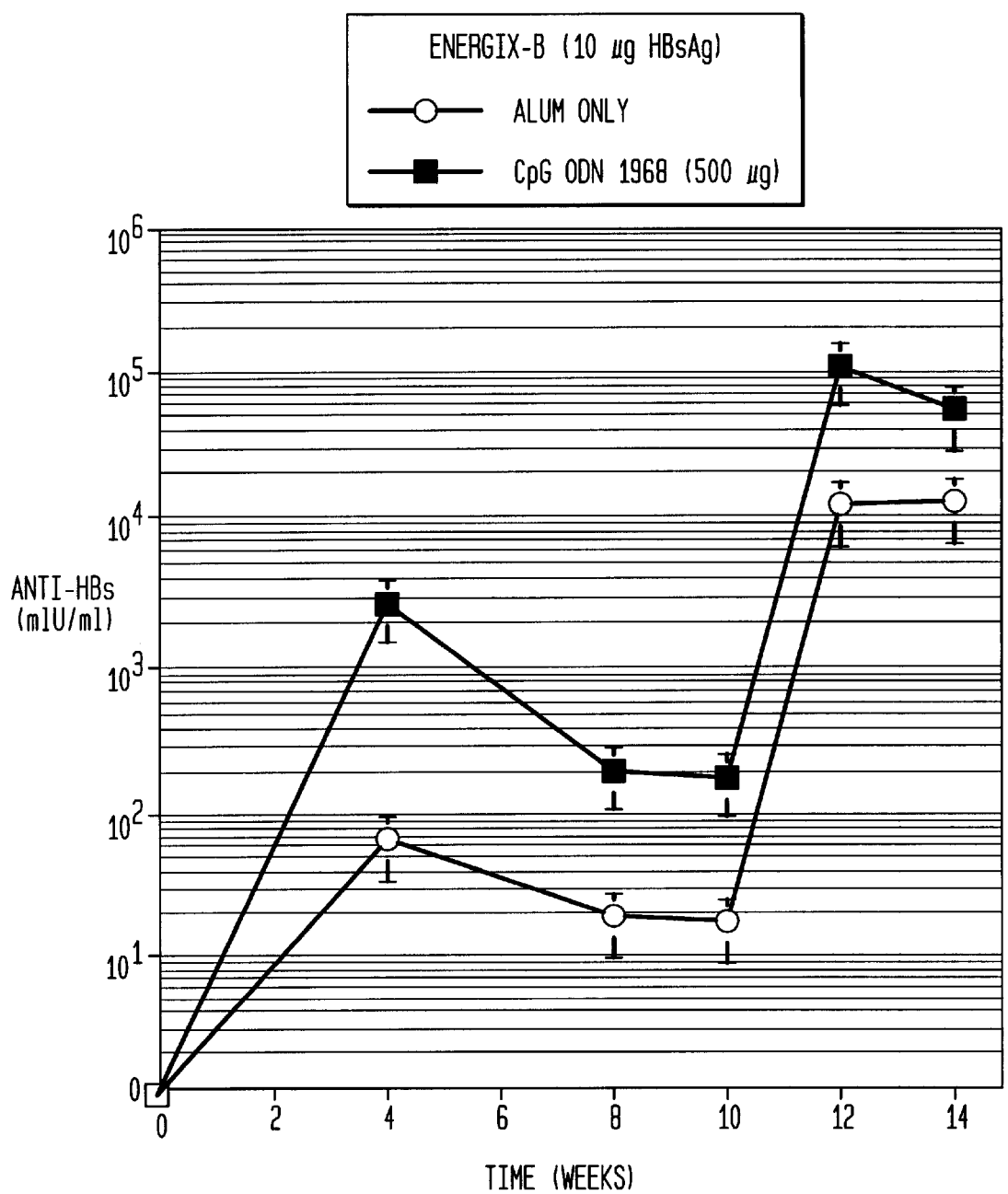
FIG. 11 is a graph of humoral responses in juvenile Cynomolgus monkeys immunized with Engerix-B vaccine (10 μg recombinant HBsAg protein with alum, SmithKline Beecham biologicals, Rixensart, BE) or with Engerix-B plus 500 μg of CpG ODN 1968. Each point represents the group mean (n=5) for anti-HBs titers in milli-International units/ml (mIU/ml). A titer of 10 mIU/ml is considered protective in humans.

The strong Th1 bias with CpG is even more evident in neonatal and young mice, which are known to naturally have a strong Th2-bias to their immune system. In this case, neither alum nor CpG ODN on their own induced detectable IgG2a, indicating a very poor or absent Th1 response. Remarkably, when used together, CpG ODN and alum induced high levels of Ig G2a antibodies, which were now the predominant form of IgG (FIG. 10). Similarly, neither CpG ODN or alum induced significant levels of CTL in young mice, yet when used together there was a strong CTL response, that was even stronger than obtained with a DNA vaccine (FIG. 9).

Figure 4:
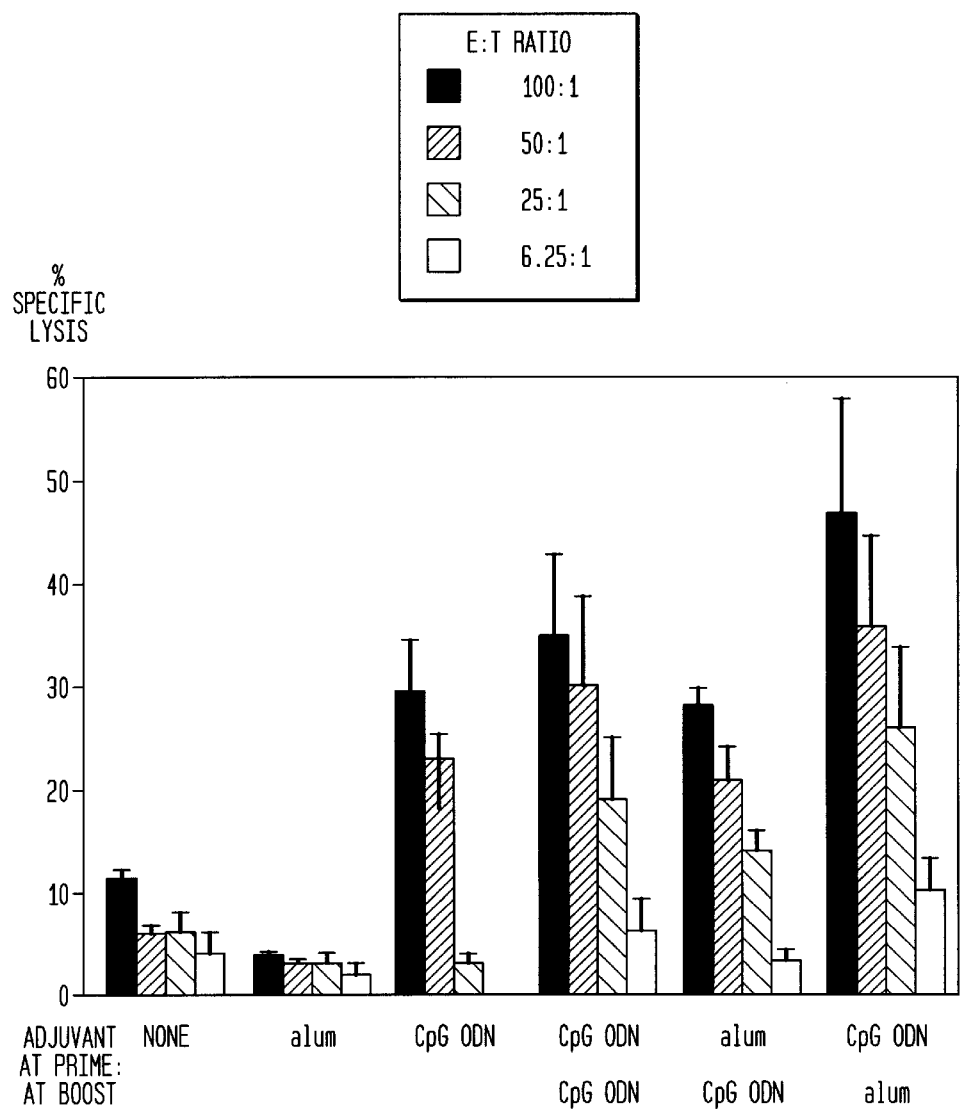
FIG. 4 is a graph of CTL responses in adult BALB/c mice immunized with 1 μg recombinant HBsAg protein with alum (25 mg Al$^{3+}$/mg HBs/Ag), with 10 μg of CpG ODN 1826, or with both alum and CpG ODN. Some animals were boosted with the same or a different formulation after 8 weeks. Each point represents the group mean (n=5) for % specific lysis of HBsAg-expressing target cell at various effector:target (E:T) cell ratios.

The strength of the Th1 influence of CpG ODN is seen not only by its ability to dominate over the Th2 effect of alum when they are co-administered, but also to induce Th1 responses in animals previously primed for a Th2 response with alum. Immunization with HBsAg using alum as an adjuvant completely abrogates the CTL response owing to the strong Th2 bias of alum (FIGS. 1 and 4). However, in mice using alum at prime and CpG at boost, good CTL were induced, indicating the possibility of CpG to overcome a previously established Th2 response (FIG. 4).

Aluminum hydroxide (alum) is currently the only adjuvant approved for human use. An important disadvantage of alum is that it induces a Th2- rather than a Th1-type immune response, and this may interfere with induction of CTL. Indeed, in mice immunized with recombinant HBsAg, the addition of alum selectively blocked activation of CD8$^+$ CTL (Schirmbeck et al., 1994). Although not essential for protective immunity against HBV, CTL may nevertheless play an important role. For example, a lack of HBV-specific CTL is thought to contribute to the chronic carrier state. In contrast, one of the primary advantages of CpG DNA over alum as an adjuvant is the Th1-bias of the responses and thus the possibility to induce CTL. A striking finding from the present study is that CpG can completely counteract the Th2-bias of alum when the two adjuvants are delivered together, and in the case of immunization in early life, the combination can even give a more Th1 response than CpG ODN alone. This could allow one to capitalize on the strong synergistic action of the two adjuvants on the humoral response while still allowing CTL in adults, and to induce a stronger Th1 response in infants.

The use of alum has been linked to Th2-type diseases. The much higher prevalence of asthma (another Th2-type disease) in more highly developed nations may be linked to the high hygiene level and rapid treatment of childhood infections (Cookson and Moffatt, 1997). Early exposure to bacterial DNA (and immunostimulatory CpG motifs) pushes the immune system away from Th2- and towards a Th1-type response and this may account for the lower incidence of asthma in less developed countries, where there is a much higher frequency of upper respiratory infections during childhood. Addition of CpG ODN as adjuvant to all pediatric vaccines could re-establish a Th1-type response thereby reducing the incidence of asthma.

Example 4

Synergy of CpG ODN with Other Adjuvants for Induction of a Th1-type Immune Responses The synergistic effect of CpG ODN on Th1 responses was also seen using other adjuvants. IFA on its own induces a very strong Th2-type response with virtually no IgG2a antibodies (IgG2a:IgG1=0.002) and CpG ODN on its own induces a moderate Th1 response (IgG2a:IgG1=1.4), but together the response was very strongly Th1 (IgG2a:IgG1=24.0). It is notable that this is even more Th1 than the response induced by CFA (ratio=0.5) (FIG. 6).

Similarly, CpG and MPL on their own are moderately Th1 (IgG2a:IgG1 ratios at 4 weeks are 1.4 and 1.9 respectively), but together are very strongly Th1 with a large predominance of IgG2a antibodies (ratio=83.3)(FIG.7).

Example 5

CpG ODN as Synergistic Adjuvant in Cynomolgus Monkeys

CpG ODN, in combination with alum, also acts as a potent adjuvant to augment anti-HBs responses in Cynomolgus monkeys. Compared to responses obtained with the commercial HBV vaccine that contains alum, monkeys immunized with the commercial vaccine plus CpG ODN attained titers 50-times higher after prime and 10-times higher after boost (FIG. 14).

Example 6

CpG ODN as Synergistic Adjuvant to HBsAg in Hyporesponder Orangutans

The orangutans, a great ape very closely related to man, can be naturally infected with HBV in a manner similar to humans. Unfortunately, orangutans are hyporesponsive to the commercial HBV vaccine that contains alum as an adjuvant. Compared to humans, where 13% and 56% of vaccinated individuals seroconvert by 4 weeks after first and second doses respectively (Yano and Tashiro, 1988), only 0% and 15% of vaccinated orangutans have seroconverted by the same times. With the addition of 1 mg CpG ODN, this becomes 43% and 100% respectively. A synergistic response is seen even in these hyporesponders, because antibody levels and seroconversion rates are better with CpG ODN plus alum than with either adjuvant alone (FIG. 12).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

REFERENCES

1. Chen D. S. et al. (1996). *Cancer Causes& Control* 7:305–311.
2. Cookson, W. O. C. M. & Moffatt, M. F. (1997). *Science* 275: 41–42.
3. Cowdery, J. S. et al. (1996). *J. Immunol.* 156: 4570.
4. Davis, H. L. et al. (1993). *Human Molec. Genet.* 2: 1847–1851.
5. Davis, H. L. et al. (1995). *Human Gene Ther.* 6: 1447–1456.
6. Davis, H. L. et al. (1996). *Proc. Natl. Acad Sci. USA* 93: 7213–7218.
7. Davis, H. L. et al. (1996). *Vaccine* 14: 910–915.

8. Davis, H. L. et al. (1997). *Gene Ther. (in press)*.
9. Davis, H. L. & Brazolot Millan, C. L. (1997). *Blood Cell Biochem. (in press)*
10. Donnelly, J. J. et al. (1996). *Life Science*. 60: 163–172.
11. Dubois, M.-F. et al. (1980). *Proc. Natl. Acad. Sci. USA* 77: 4549–4553.
12. Ellis, R. W. (Ed.) (1993). *Hepatitis B Vaccines in Clinical Practise*. New York: Marcel-Dekker.
13. Halpem, M. D. et al. (1996). *Cell. Immunol*. 167: 72.
14. Klinman, D. M. et al. (1996). *Proc. Natl. Acad Sci. USA* 93: 2879–2883.
15. Krieg, A. M. et al. (1995). *Nature* 374: 546–549.
16. Kruskall, M. S. et al. (1992). *J. Exp. Med* 175: 495–502.
17. Lee C. Y. et al., (1989). J. Am. Med. Assoc. SEA
18. Li et al. , (1994). *J. Gen. Virol*. 75: 3673–3677.
19. Mancini, M. et al. (1996). *Proc. Natl. Acad Sci. USA* 93: 12496–12501.
20. Michel, M.-L. et al. (1984) *Proc. Natl. Acad Sci. USA* 81: 7708–7712.
21. Michel, M.-L. et al. (1995). *Proc. Natl. Acad. Sci. USA* 92: 5307–5311.
22. Milich, D. R. (1988). *Immunol. Today* 9: 380–386.
23. Niederau et al. (1996). *New Eng. J. Med*. 334: 1422–1427.
24. Pol, S. et al. (1993). C. R. *Acad. Sci*. (Paris) 316: 688–691.
25. Rehermann, B. et al. (1996). *Nature Med*. 2: 1104–1108.
26. Sato, Y., et al. (1996). *Science* 273: 352–354.
27. Schirmbeck, R. et al. (1994). *J. Immunol*. 152: 1110–1119.
28. Stevens, C. E. et al. (1987). *J. Am. Med. Assoc*. 257: 2612–2616.
29. Vogel, F. R. & Sarver, N. (1995). *Clin. Microbiol. Rev*. 8: 406–410.
30. Yano, M and Tashiro, A. (1988) In: Viral Hepatitis and Liver Disease, Ed: A. J. Zuckerman; Alan R. Liss, New York, pp 1038–1042.

All references, patents and patent publications that are recited in this application are incorporated in their entirety herein by reference.

We claim:

1. A composition of a synergistic combination of adjuvants, comprising:
an effective amount for inducing a synergistic adjuvant response of a combination of adjuvants, wherein the combination of adjuvants includes at least one oligonucleotide containing at least one unmethylated CpG dinucleotide and at least one non-nucleic acid adjuvant.

2. The composition of claim 1, wherein the non-nucleic acid is an adjuvant that creates a depo effect.

3. The composition of claim 2, wherein the adjuvant that creates a depo effect is selected from the group consisting of alum, emulsion based formulations, mineral oil, non-mineral oil, water-in-oil emulsions, water-in-oil-in-water emulsions, Seppic ISA series of Montanide adjuvants; MF-59; and PROVAX.

4. The composition of claim 1, wherein the non-nucleic acid adjuvant is an immune stimulating adjuvant.

5. The composition of claim 4, wherein the immune stimulating adjuvant is selected from the group consisting of saponins, PCPP polymer; derivatives of lipopolysaccharides, MPL, MDP, t-MDP, OM-174 and Leishmania elongation factor.

6. The composition of claim 1, wherein the non-nucleic acid adjuvant is an adjuvant that creates a depo effect and stimulates the immune system.

7. The composition of claim 6, wherein the adjuvant that creates a depo effect and stimulates the immune system is selected from the group consisting of ISCOMS, SB-AS2, AS2, SB-AS4, non-ionic block copolymers and SAF.

8. The composition of claim 1, wherein the composition also includes an antigen that is selected from the group consisting of peptides, polypeptides, cells, cell extracts, polysaccharides, polysaccharide conjugates, lipids, glycolipids, carbohydrates, viruses, viral extracts and antigens encoded within nucleic acids.

9. The composition of claim 8, wherein the antigen is derived from an infectious agent selected from the group consisting of a virus, bacterium, fungus and parasite.

10. The composition of claim 8, wherein the antigen is a tumor antigen.

11. The composition of claim 8, wherein the antigen is an allergen.

* * * * *